(12) United States Patent
Gershengorn et al.

(10) Patent No.: US 6,403,305 B1
(45) Date of Patent: *Jun. 11, 2002

(54) METHODS OF IDENTIFYING PEPTIDE AGONISTS OR NEGATIVE ANTAGONISTS OF A G PROTEIN COUPLED RECEPTOR

(75) Inventors: Marvin C. Gershengorn, New York; Elizabeth Geras-Raaka, Dobbs Ferry; Daniel R. Nussenzveig, New York, all of NY (US)

(73) Assignee: Cornell Research Foundation, Inc., Ithaca, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/795,876

(22) Filed: Feb. 6, 1997

(51) Int. Cl.⁷ .......................... C12Q 1/68; C12P 21/04; C12N 15/09
(52) U.S. Cl. .................. 435/6; 435/69.2; 435/69.7; 435/DIG. 6; 435/DIG. 26
(58) Field of Search ....................................... 435/7.1, 6

(56) References Cited

U.S. PATENT DOCUMENTS

| | | |
|---|---|---|
| 5,087,564 A | 2/1992 | Mai et al. |
| 5,384,243 A | 1/1995 | Gutkind et al. |
| 5,385,831 A | 1/1995 | Mulvihill et al. |
| 5,403,484 A | 4/1995 | Ladner et al. |
| 5,436,128 A | 7/1995 | Harpold et al. |
| 5,462,856 A | 10/1995 | Lerner et al. |
| 5,476,781 A | 12/1995 | Moyer et al. |
| 5,482,835 A | 1/1996 | King et al. |
| 5,498,530 A | 3/1996 | Schatz et al. |
| 5,506,102 A | 4/1996 | McDonnell |
| 5,508,384 A | 4/1996 | Murphy et al. |
| 5,514,545 A * | 5/1996 | Eberwine .................. 435/6 |
| 5,516,889 A | 5/1996 | Hollenberg et al. |
| 5,521,295 A | 5/1996 | Pacifici et al. |
| 5,565,325 A | 10/1996 | Blake |
| 5,925,529 A | 7/1999 | Coughlin et al. |

OTHER PUBLICATIONS

Chen et al. Tethered ligand library for discovery of petide agonists. The Journal of Biological Chemisry. 270:23398–23401. 1995.*

Nanevicz et al. Throbin receptor activating mutations. The Journal of Bioogical Chemistry. 271:702–706. 1996.*

Julius et al., "Molecular Characterization of a Functional cDNA Encoding the Serotonin 1 c Receptor," *Science*, 241:558–64 (1988).

Wright et al., "Cloning Strategies for Peptide Hormone Receptors," *Acta. Endocrinol.*, 125:97–104 (1992).

Burbach et al., "The Structure of Neuropeptide Receptors," *European J. Pharm–Mol. Pharm. Sec.*, 227:1–18 (1992).

Chen et al., "Tethered Ligand Library for Discovery of Peptide Agonists," *J. Biol. Chem.*, 270(40):23398–23401 (1995).

Perez et al., Human Formyl Peptide Receptor Ligand Binding Domain(s), *J. Biol. Chem.*, 269(36):22485–22487 (1994).

Horvat et al., "The Functional Thrombin Receptor is Associated with the Plasmalemma and a Large Endosomal Network in Cultured Umblical Vein Endothelial Cells," *J. Cell Science*, 106:1155–1164 (1995).

Stroop et al., "Chimeric Human Calcitonin and Glucagon Receptors Reveal Two Dissociable Calcitonin Interaction Sites," *Biochemistry*, 34:1050–1057 (1995).

Price et al., "Functional Coupling of a Mammalian Somatostatin Receptor to the Yeast Pheromone Response Pathway," *Mol. and Cell. Biol.*, 15(11):6188–6195 (1995).

Tsou et al., "A β2RARE–LacZ Transgene Identifies Retinoic Acid–Mediated Transcriptional Activation in Distinct Cutaneous Sites," *Experimental Cell Research*, 214:27–34 (1994).

Tate et al., "Secreted Alkaline Phosphatase: An Internal Standard for Expression of Injected mRNAs in the Xenopus oocyte," *FASEB J.*, 4:227–231 (1990).

Laakkonen et al., "A Refined Model of the Thryrotropin–Releasing Hormone (TRH) Receptor Binding Pocket. Novel Mixed Mode Monte Carlo/Stochastic Dynamics Simulations of the Complex between TRH and TRH Receptor," *Biochemistry*, 35(24):7651–7663 (1996).

(List continued on next page.)

*Primary Examiner*—Padmashri Ponnaluri
*Assistant Examiner*—Thomas Prasthofer
(74) *Attorney, Agent, or Firm*—Nixon Peabody LLP

(57) ABSTRACT

The present invention is directed to a strategy to discover small peptides that will activate any G protein coupled receptor (GPCR) or inactivate any constitutively active GPCR. The strategy uses combinatorial peptide libraries to screen millions of random peptides for agonist/negative antagonist activity. The method of the subject invention comprises expressing a peptide of a peptide library tethered to a G protein coupled receptor of interest in a cell, and monitoring the cell to determine whether the peptide is an agonist or negative antagonist of the GPCR of interest. The peptide is tethered to the GPCR by replacing the amino terminus of the GPCR with the amino terminus of a self-activating receptor, and replacing the natural peptide ligand present in the amino terminus of the self-activating receptor with the peptide of the peptide library. In one embodiment for discovery of agonists, a ligand of the self-activating receptor is used to cleave the resulting amino terminus to expose the peptide of the peptide library. In another embodiment for discovery of agonists or negative antagonists, the GPCR construct ends at the peptide so the peptide is always exposed. Preferably, the self-activating receptor is the thrombin receptor and the ligand of the self-activating receptor is thrombin.

21 Claims, 7 Drawing Sheets

OTHER PUBLICATIONS

Gundersen et al., "Neural Regulation of Muscel Acetylcholine Receptor γ–and β–Subunit Gene Promoters in Transgenic Mice," *J. Cell Biol.*, 123(6):1535–1544 (1993).

Heinflink et al., "A Constitutively Active Mutant Thyrotropin–Releasing Hormone Receptor Is Chronically Down–Regulated in Pituitary Cells: Evidence Using Chlordiazepoxide as a Negative Antagonist," *Mol. Endocrin.*, 9(11):1455–1460 (1995).

Hersh et al., "Modulation of Gene Expression after Replication–Deficient, Recombinant Adenovirus–Mediated Gene Transfer by the Product of a Second Adenovirus Vector," *Gene Therapy*, 2:124–131 (1995).

Yan et al., "Multiple Regions of NSRI Are Sufficient for Accumulation of a Fusion Protein within the Nucleolus," *J. Cell Biol.*, 123(5):1081–1091 (1993).

Tapparelli et al., "Structure and Function of Thrombin Receptors," *TiPs*, 14:426–428 (1993).

Gershengorn et al., "Molecular and Cellular Biology of Thyrotropin–Releasing Hormone Receptors," *Physiological Reviews*, 76(1):175–191 (1996).

Cascieri et al., "Molecular Characterization of a Common Binding Site for Small Molecules Within the Transmembrane Domain of G–Protein Coupled Receptors," *J. Pharma. and Toxicol. Methods*, 33:179–185 (1995).

* cited by examiner

METHODS OF IDENTIFYING PEPTIDE AGONISTS OR NEGATIVE ANTAGONISTS OF A G PROTEIN COUPLED RECEPTOR

The subject matter of this application was made with support from the United States Government under grant Nos. DK43036, DK46652, and DK50673 of the National Institutes of Health.

FIELD OF THE INVENTION

The present invention relates to drug discovery, and more particularly to a strategy to clone drugs for G protein coupled receptors.

BACKGROUND OF THE INVENTION

Throughout this application various publications are referenced, many in parenthesis. Full citations for these publications are provided at the end of the Detailed Description. The disclosures of these publications in their entireties are hereby incorporated by reference in this application.

It has been estimated that more than 50% of the drugs in clinical use today are directed at G protein coupled receptors (GPCRs). Small peptides can activate a number of receptors of this family, such as receptors for thyrotropin-releasing hormone (TRH), which is a tripeptide (Gershengorn and Osman 1996), thrombin, for which a hexapeptide is a full agonist (Tapparelli et al. 1993), and formyl-Met-Leu-Phe, which is a tetrapeptide (Perez et al. 1994). Small molecules can inactivate constitutively active GPCRs, such as benzodiazepines, which inactivate TRH receptor mutants that are constitutively active (Heinflink et al. 1995)(a constitutively active receptor is one that signals in the absence of agonist).

It appears that these small molecules interact primarily, if not exclusively, with the transmembrane (TM) bundle or extracellular (EC) loops of GPCRs (Cascieri et al. 1995). For example, it appears that the "activation domain" of a GPCR with a large EC amino terminus, such as the receptor for calcitonin, is present within the region of the receptor from the beginning of TM helix one to the C-terminus, which includes the TM bundle and EC loops (Stroop et al. 1995).

The discovery of peptides that could activate GPCRs or inactivate constitutively active GPCRs may have enormous potential for clinical applications because a number of peptide agonists of GPCRs are currently used therapeutically and diagnostically. In the shorter term, the discovery of such peptides will yield reagents that could be used by pharmaceutical companies to identify ligands for or functions of "orphan" receptors.

SUMMARY OF THE INVENTION

To this end, it is an object of the subject invention to provide a strategy to discover small peptides that will activate any G protein-coupled receptor (GPCR) or inactivate any constitutively active GPCR. These peptides could serve as lead chemicals for design of clinically useful drugs or could be used to identify the natural ligand or physiologic function of "orphan" receptors, that is, putative receptors that have been identified (i.e., cloned) but for which the function is unknown. The strategy uses combinatorial peptide libraries tethered to the GPCR. With this approach, millions of random peptides of a given length can be tested for activity in the context of a library and those that activate GPCRs or inactivate constitutively active GPCRs can be identified.

The invention thus provides a method of identifying peptide agonists or negative antagonists of a G protein coupled receptor of interest. The method comprises expressing a peptide of a peptide library tethered to a G protein coupled receptor of interest in a cell, and monitoring the cell to determine whether the peptide is an agonist or negative antagonist of the G protein coupled receptor of interest.

In one embodiment for identifying peptide agonists, the expression of a peptide of a peptide library tethered to a G protein coupled receptor of interest in a cell comprises preparing a G protein coupled receptor construct, introducing the G protein coupled receptor construct into a cell, allowing the cell to express the G protein coupled receptor encoded thereby, and exposing the cell to a ligand of a self-activating receptor, wherein the ligand cleaves the G protein coupled receptor construct so as to expose the inserted peptide of the peptide library. The G protein coupled receptor construct for identifying a peptide agonist, which is also provided by the subject invention, comprises a nucleic acid molecule encoding a G protein coupled receptor with a deleted first amino terminus; a nucleic acid molecule encoding a second amino terminus of a self-activating receptor attached to the nucleic acid molecule encoding the G protein coupled receptor at the deleted first amino terminus, the second amino terminus having a deleted portion which is a peptide agonist for activating the self-activating receptor; and a nucleic acid molecule encoding the peptide of the peptide library inserted into the second amino terminus and replacing the deleted portion.

In a further embodiment for identifying peptide negative antagonists, the G protein coupled receptor of interest is a constitutively active G protein coupled receptor and the expression of a peptide of a peptide library tethered to the G protein coupled receptor of interest in a cell comprises preparing a constitutively active G protein coupled receptor construct, introducing the constitutively active G protein coupled receptor construct into a cell, and allowing the cell to express the constitutively active G protein coupled receptor encoded thereby. The constitutively active G protein coupled receptor construct for identifying a peptide negative antagonist, which is also provided by the subject invention, comprises a nucleic acid molecule encoding a constitutively active G protein coupled receptor with a deleted first amino terminus; a nucleic acid molecule encoding a second amino terminus of a self-activating receptor attached to the nucleic acid molecule encoding the constitutively active G protein coupled receptor at the deleted first amino terminus, the second amino terminus having a deleted portion which includes a peptide agonist for activating the self-activating receptor as well as any amino acids positioned amino terminally to the peptide agonist; and a nucleic acid molecule encoding the peptide of the peptide library inserted into the second amino terminus and replacing the deleted portion.

In a still further embodiment for identifying peptide agonists, the expression of a peptide of a peptide library tethered to a G protein coupled receptor of interest in a cell comprises preparing a G protein coupled receptor construct, introducing the G protein coupled receptor construct into a cell, and allowing the cell the express the G protein coupled receptor encoded thereby. The G protein coupled receptor construct for identifying a peptide agonist, which is also provided by the subject invention, comprises a nucleic acid molecule encoding a G protein coupled receptor with a deleted first amino terminus; a nucleic acid molecule encoding a second amino terminus of a self-activating receptor attached to the nucleic acid molecule encoding the G protein coupled receptor at the deleted first amino terminus, the second amino terminus having a deleted portion which includes a peptide agonist for activating the self-activating receptor as well as any amino acids positioned amino terminally to the peptide agonist; and a nucleic acid molecule encoding the peptide of the peptide library inserted into the second amino terminus and replacing the deleted portion.

BRIEF DESCRIPTION OF THE DRAWINGS

These and other features and advantages of this invention will be evident from the following detailed description of preferred embodiments when read in conjunction with the accompanying drawings in which.

DETAILED DESCRIPTION

Figure 1:
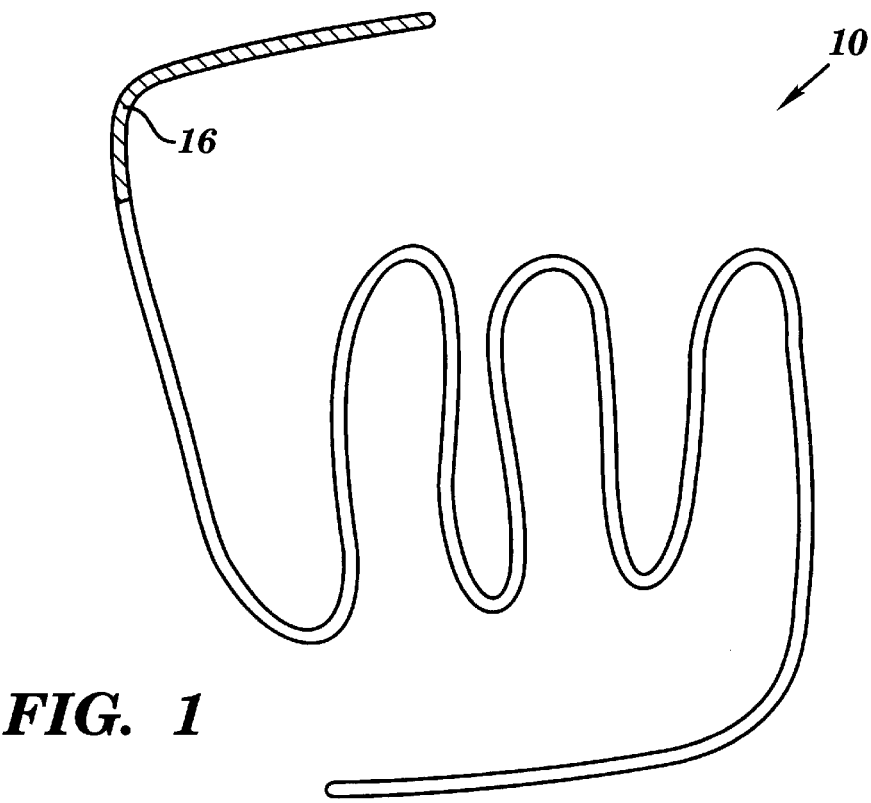
FIG. 1 is a diagram of a G protein coupled receptor.

The invention provides a strategy that is designed to discover small peptides that will activate any G protein-coupled receptor (GPCR) or inactivate any constitutively active GPCR. A constitutively active receptor is one that signals in the absence of an agonist. These peptides could serve as lead chemicals for design of clinically useful drugs or could be-used to identify the natural ligand or physiologic function of "orphan" receptors, that is, putative receptors that have been identified (cloned) but for which the function is unknown. The discovery of peptides that could serve these functions may be accomplished with an approach that uses combinatorial peptide libraries. With this approach, millions of random peptides of a given length are tested for activity in the context of a library and those that activate GPCRs or inactivate constitutively active GPCRs are discovered. As stated above, this approach may have enormous potential for clinical applications because a number of peptide agonists of GPCRs are currently used therapeutically and diagnostically. In the shorter term, however, this technology will yield reagents that could be used by pharmaceutical companies to identify ligands for or functions of "orphan" receptors.

To discover small peptides that can serve as agonists for GPCRs, a combinatorial peptide library is constructed that expresses random pentapeptides tethered to the seven TM helical bundle of any GPCR. A pentapeptide library was chosen based on the fact that TRH is a tripeptide that is blocked at both ends (3+2 (for block)=5) and the resulting number of clones is workable.

The library contains all 20 natural amino acids at each of the five positions and therefore has a complexity of $20^5 =$ $3.2 \times 10^6$ possible combinations. To this end the complementary DNA (cDNA) sequence that normally encodes any GPCR's N-terminal EC domain is substituted by a DNA sequence that encodes the N-terminal ectodomain of a self-activating receptor such as the thrombin receptor. Thrombin receptor (ThrR) is a GPCR that is activated by a mechanism that is different from most GPCRs. Thrombin is a serine protease that binds to and cleaves its receptor's N-terminal end at a specific site, exposing a new N-terminus that acts as a peptide agonist tethered to the remainder of the receptor molecule. The chimeric ThrR/GPCR has the variable pentapeptide sequence substituting for the native peptide sequence that is normally unmasked by thrombin action and constitutes the ThrR peptide agonist, but retains thrombin binding sequences and the thrombin-specific cleavage site. Therefore, the N-terminus of expressed receptors is cleaved by thrombin at the appropriate location exposing a new N-terminus that is made of the variable pentapeptide segment of the library tethered to the remainder of the GPCR. As used herein, a receptor that operates in this manner is referred to as a self-activating receptor since a ligand of the receptor cleaves the receptor to expose a natural peptide agonist which activates the receptor. Thrombin is the most well known of such self-activating receptors, but the invention can be readily practiced using other such receptors (e.g., the protease activated receptor or a synthetic receptor).

The cDNA sequence encoding the new N-terminus of the chimeric ThrR/GPCR, consisting of a prolactin leader or signal peptide, followed by the FLAG epitope, followed by the N-terminus of the mature human ThrR, where the pentapeptide library is constructed, is constructed by gene synthesis. The cDNA sequence consists of a DNA segment of approximately 300 base pairs encoding 100 amino acids that is ligated in frame through an appropriate restriction endonuclease cleavage site created by polymerase chain reaction (PCR) in the cDNA of any GPCR at a position encoding the amino acids that constitute the transition between the N-terminus and the first TM domain. After ligation into a mammalian expression vector, *Escherichia coli* is transformed by electroporation and the transformants are subdivided into pools whose maximal workable complexity is determined according to the efficiency of mammalian cell transfection and/or sensitivity of the detection system.

Amplified reporter systems based on the second messenger systems triggered by the GPCR are used. For discovery of agonists, the assay is based on gene induction in COS-1 cells using β-galactosidase as a reporter gene in a single cell assay. This assay takes advantage of the amplification of the enzyme activity of the reporter, with an easily determined color reaction as endpoint, and of the expression of a single receptor clone with its tethered agonist in COS-1 cells because of replication of the plasmids introduced. The signal is increased because the construct used has a nuclear localization signal ligated to the β-galactosidase that allows the protein to concentrate in the nucleus (Hersh et al. 1995). Single clones that exhibit activation of chimeric ThrR/GPCR after thrombin addition to cleave the N-terminus and expose the tethered agonist, as measured by increased color reaction, are isolated using sib selection, which consists of successive subdivision and amplification of positive pools of clones. A number of other reporter systems can also be used. These include, but are not limited to, analysis of acute effects of agonist using Xenopus laevis oocytes in which one measures changes in membrane conductance —using calcium-activated chloride conductance for phosphoinositide (PI) cascade or cAMP-activated chloride conductance through cystic fibrosis transmembrane regulator (CFTR) that is co-expressed for cAMP cascade; induction of genes in COS-1 cells that yield protein products that are displayed in the cytoplasm or on the surfaces of cells and visualized by immunofluorescence (by microscopy or fluorescence activated cell sorting) or immunocytochemistry; and analysis of acute effects on elevation of cytoplasmic calcium using fluorescence indicators.

To discover small peptides that can serve as agonists or small peptides that can serve as negative antagonists (or inverse agonists) for GPCRs, a second type of combinatorial peptide library is constructed that expresses random pentapeptides tethered to the seven TM helical bundle of a given GPCR that is different from the one described above to discover agonists but is based on the same principles. This library also contains all 20 natural amino acids at each of the five positions and therefore has a complexity of $20^5 3.2 \times 10^6$ possible combinations. In this library, however, the cDNA sequence that normally encodes GPCR's N-terminal EC domain is substituted by a DNA sequence that encodes the self-activating receptor's (e.g., thrombin's) N-terminal ectodomain but without the domain that usually is cleaved to reveal the tethered peptide. In this library, the chimeric ThrR/GPCR has the variable pentapeptide sequence substituting for the native peptide sequence that is normally unmasked by thrombin action exposed as the N-terminus of all receptors. Therefore, the N-terminus of expressed receptors is a random pentapeptide that can act as an agonist of a GPCR or as a negative antagonist with regard to the constitutive activity of some GPCRs. With regard to the negative antagonists, in contrast to looking for stimulation of a GPCR signalling response, monitoring is for inactivation of a "basal" activity.

A two-reporter system is used for discovery of negative antagonists. The second reporter gene is used to identify cells that have been transfected and are expressing foreign proteins and to distinguish them from cells that have not been transfected and are not expressing foreign proteins. This is a crucial distinction for this approach because differentiation between cells that have the capacity to express the specific reporter gene but are not because transcription has been inhibited and cells that are not expressing the reporter gene because they are not transfected is necessary. The same reporter genes for GPCR-specific effects as for the discovery of agonist peptides are used. The nonspecific reporter for transfection is a construct containing a mutant of the human placental alkaline phosphatase gene (Tate et al. 1990) that is targeted to the cytoplasm under the control of a cytomegalovirus promoter. Thus, one can monitor for 3 types of cells: 1) cells in which β-galactosidase is expressed at high levels in the nucleus and alkaline phosphatase is expressed in the cytoplasm—these are transfected cells that do not express receptors that contain a peptide that has negative antagonistic activity because expression of β-galactosidase is induced by the constitutive signalling activity of the GPCR; 2) cells in which β-galactosidase is not expressed in the nucleus and alkaline phosphatase is not expressed in the cytoplasm—these are cells that have not been transfected; and 3) cells in which β-galactosidase is not expressed or is expressed at low levels in the nucleus and alkaline phosphatase is expressed in the cytoplasm—these are transfected cells that express receptors that contain a peptide that has negative antagonistic activity. The approach to sib selection is identical to that outlined above.

A yeast (*Saccharomyces cerevisiae*) bioassay system that is responsive to activation of GPCRs or to inactivation of constitutively active GPCRs can also be used to screen the tethered, combinatorial peptide library. This bioassay is based on the finding that mammalian GPCRs expressed in yeast will regulate the endogenous signal transduction cascades (Dohlman et al. 1991), in particular the pathway for regulation of proliferation (King et al. 1990). A sensitive and specific yeast expression system permits powerful genetic selection methods, which use modifications in the endogenous pheromone response pathways (Price et al. 1995; Price et al. 1996), to be developed for use with the screening methods of the subject invention. The pheromone signalling cascade in yeast uses one of two GPCRs {for (STE2) or a mating factor (STE3)} to couple to a heterotrimeric G protein, which is comprised of (GPA1), (STE4) and (STE18) subunits, to activate a protein kinase signalling cascade that leads to cell cycle arrest, which is mediated by FAR1, and activation of pheromone-responsive genes, such as FUS1. SST2 is another important member of this signalling pathway because it serves to desensitize (or "turn off") the pathway. Several members of this pathway can be modified to improve the sensitivity and assay of GPCRS. This system provides markedly greater ease of assay and permits the screening of hundreds of thousands of recombinant GPCR clones simultaneously. Systems can be developed that can be used to screen for agonist and negative antagonist probes/drugs. The major advantage of this type of assay system over those usually employed to screen numerous potential probes/drugs rapidly, which is necessary for the application of the method of the subject invention, is that it relies on a response in a single yeast cell and will identify the responsive cell in a population of millions of cells.

One assay will be a minor modification of the previously published yeast expression system to assay for activation of GPCRs in which FAR1 and SST2 genes were inactivated and a FUS1-HIS3 gene is used for selection of cells expressing activated GPCRs on a medium deficient in histidine (Price et al. 1995). The changes will involve only adapting the system so that it will allow high efficiency transformation of yeast cells with a library that contains 3.2 million different GPCRs. The second assay will be modified more extensively so that it will measure constitutively activated GPCRs that are inactivated. One approach to this type of assay will involve using yeast cells in which the FAR1 gene is intact so that constitutively active GPCRs will cause cells to be arrested in the cell cycle. Cells in which the GPCR has been inactivated will not exhibit growth arrest but will proliferate as normal haploid cells in the absence of mating factor.

The invention thus provides a method of identifying peptide agonists or negative antagonists of a G protein coupled receptor of interest. The method comprises expressing a peptide of a peptide library tethered to a G protein coupled receptor of interest in a cell, and monitoring the cell to determine whether the peptide is an agonist or negative antagonist of the G protein coupled receptor of interest.

In one embodiment for identifying peptide agonists, the expression of a peptide of a peptide library tethered to a G protein coupled receptor of interest in a cell comprises preparing a G protein coupled receptor construct, introducing the G protein coupled receptor construct into a cell, allowing the cell to express the G protein coupled receptor encoded thereby, and exposing the cell to a ligand of a self-activating receptor, wherein the ligand cleaves the G protein coupled receptor construct so as to expose the inserted peptide of the peptide library. The G protein coupled receptor construct for identifying a peptide agonist, which is also provided by the subject invention, comprises a nucleic acid molecule encoding a G protein coupled receptor with a deleted first amino terminus; a nucleic acid molecule encoding a second amino terminus of a self-activating receptor attached to the nucleic acid molecule encoding a G protein coupled receptor at the deleted first amino terminus, the second amino terminus having a deleted portion which is a peptide agonist for activating the self-activating receptor; and a nucleic acid molecule encoding the peptide of the peptide library inserted into the second amino terminus and replacing the deleted portion.

Figure 2:
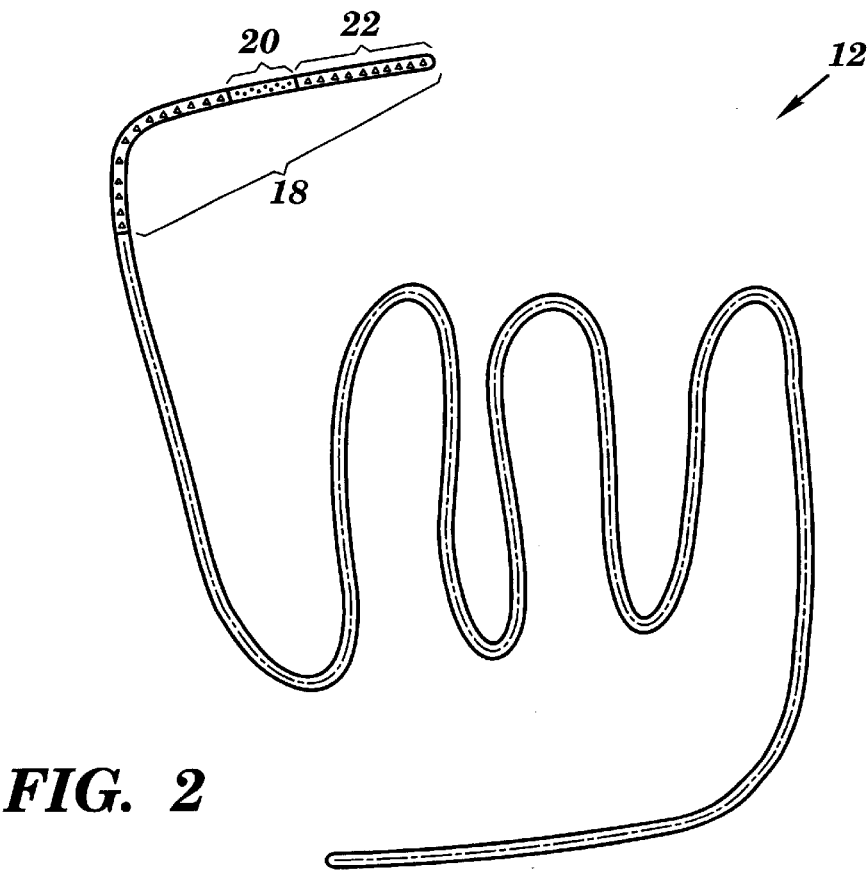
FIG. 2 is a diagram of a thrombin receptor.
Figure 3:
FIG. 3 is a diagram of a peptide of a peptide library.
Figure 4:
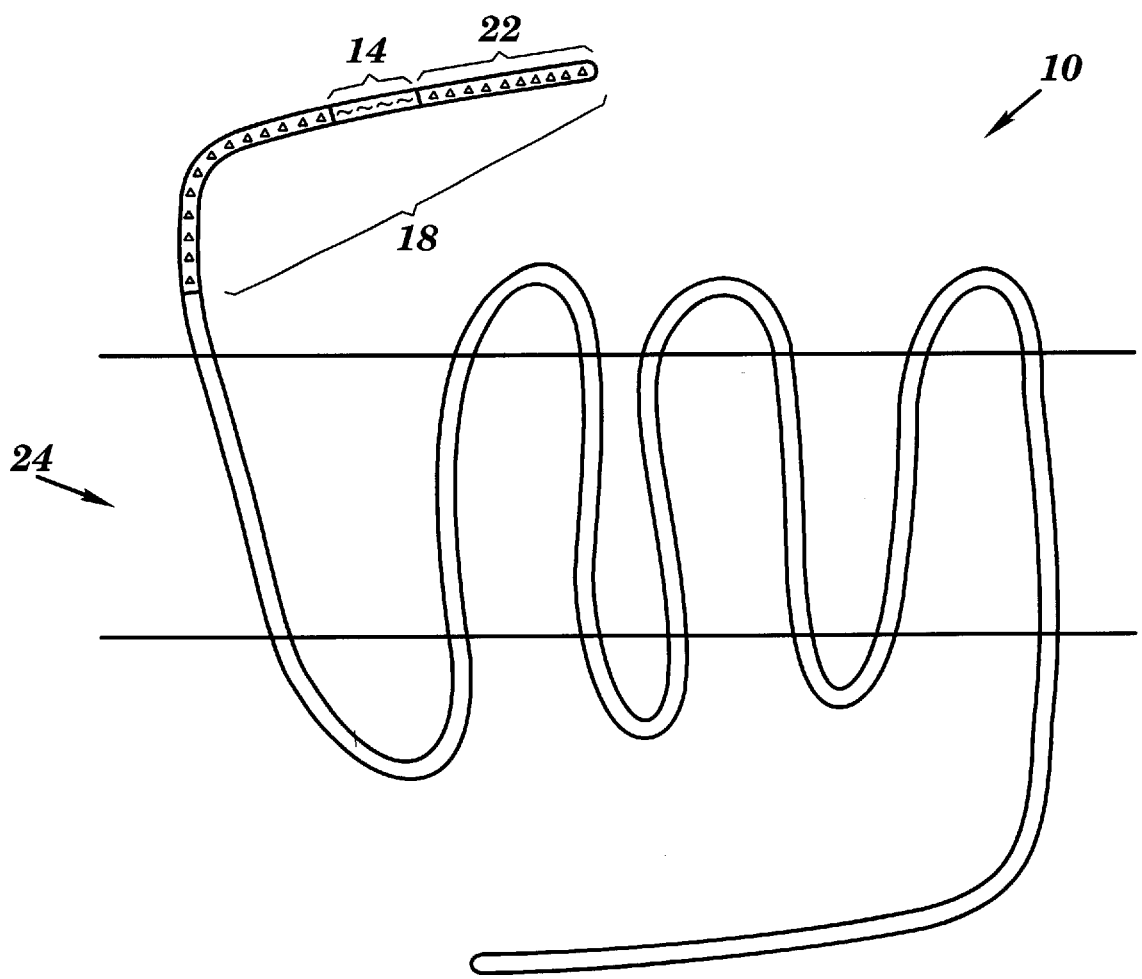
FIG. 4 is a diagram of a G protein coupled receptor construct according to the subject invention.

One embodiment of a G protein coupled receptor construct for identifying a peptide agonist of the G protein coupled receptor is shown in FIG. 4. Referring to FIGS. 1–4, the construct involves three parts based on a nucleic acid molecule encoding a G protein coupled receptor (10)(FIG. 1), a nucleic acid molecule encoding a thrombin receptor (12)(FIG. 2), and a nucleic acid molecule encoding a peptide (14) of a peptide library (FIG. 3). Referring to FIG. 1, the G protein coupled receptor (10) includes an amino terminus (16). Referring to FIG. 2, the thrombin receptor (12) also includes an amino terminus (18). Within the amino terminus (18) of the thrombin receptor (12) is a portion (20) which is a peptide agonist for the thrombin receptor. When the thrombin receptor is exposed to thrombin, thrombin cleaves the amino terminal part of the molecule (22) leaving the portion (20) which is a peptide agonist exposed. The portion (20) reacts with the remainder of the thrombin molecule and binds thereto, activating the thrombin receptor. Referring to FIG. 3, the peptide (14) of a peptide library is shown.

FIG. 4 shows one embodiment of the G protein coupled receptor construct for identifying a peptide agonist according to the subject invention positioned within a cellular membrane (24). The construct includes a nucleic acid molecule encoding the G protein coupled receptor (10) but a portion of the nucleic acid molecule which encodes the amino terminus of the receptor is deleted. In its place, the amino terminus (18) of the thrombin receptor is inserted. Within the amino terminus (18) of the thrombin receptor, the portion which is a peptide agonist has been deleted and replaced with the peptide (14) of the peptide library. Thus, the G protein coupled receptor construct has the backbone of a selected G protein coupled receptor, with an amino terminus of the thrombin receptor. However, the normal peptide agonist of the thrombin receptor has been replaced by a peptide library. Thus, when the G protein coupled receptor construct of the subject invention is exposed to thrombin, thrombin will cleave the amino terminal part (22) of the construct leaving the peptide (14) of the peptide library exposed. If the exposed peptide is an agonist of the G protein coupled receptor, the receptor will be turned on.

In a further embodiment for identifying a peptide negative antagonist, the G protein coupled receptor of interest is a constitutively active G protein coupled receptor and the expression of a peptide of a peptide library tethered to the G protein coupled receptor of interest in a cell comprises preparing a constitutively active G protein coupled receptor construct, introducing the constitutively active G protein coupled receptor construct into a cell, and allowing the cell to express the constitutively active G protein coupled receptor encoded thereby. The constitutively active G protein coupled receptor construct for identifying a peptide negative antagonist, which is also provided by the subject invention, comprises a nucleic acid molecule encoding a constitutively active G protein coupled receptor with a deleted first amino terminus; a nucleic acid molecule encoding a second amino terminus of a self-activating receptor attached to the nucleic acid molecule encoding the constitutively active G protein coupled receptor at the deleted first amino terminus, the second amino terminus having a deleted portion which includes a peptide agonist for activating the self-activating receptor as well as any amino acids positioned amino terminally to the peptide agonist; and a nucleic acid molecule encoding the peptide of the peptide library inserted into the second amino terminus and replacing the deleted portion.

Figure 5:
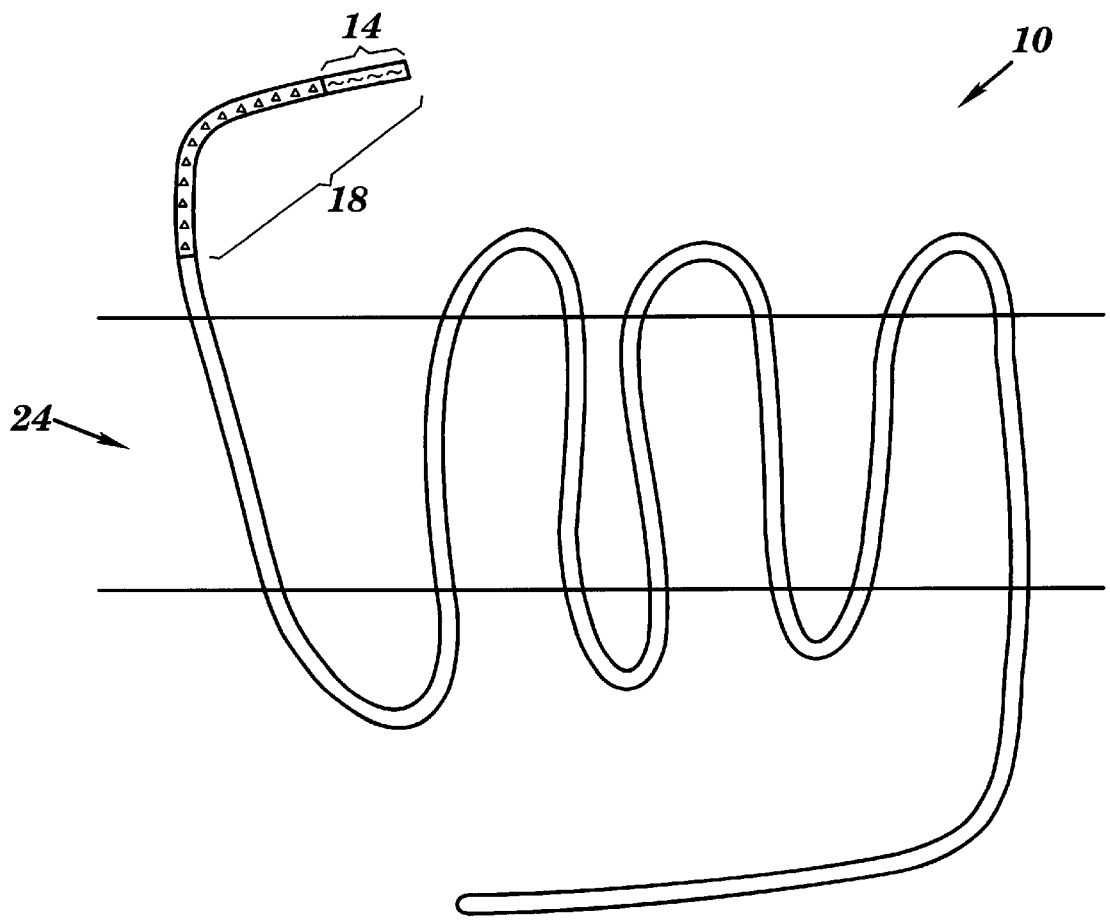
FIG. 5 is a diagram of a constitutively active G protein coupled receptor construct according to the subject invention.

The constitutively active G protein coupled receptor construct for identifying a peptide negative antagonist of the constitutively active G protein coupled receptor is shown in FIG. 5, positioned within a cellular membrane (24). The construct includes a nucleic acid molecule encoding the G protein coupled receptor (10) but a portion of the nucleic acid molecule which encodes the amino terminus of the receptor is deleted. In its place, the amino terminus (18) of the thrombin receptor is inserted. Within the amino terminus (18) of the thrombin receptor, the portion which is a peptide agonist has been deleted as well as any amino acids positioned amino terminally to the peptide agonist which are normally cleaved by thrombin, and replaced with the peptide (14) of the peptide library. Thus, the constitutively active G protein coupled receptor construct has the backbone of a selected G protein coupled receptor, with an amino terminus of the thrombin receptor. However, the normal peptide agonist of the thrombin receptor has been replaced by a peptide library and the peptide is always exposed. If the exposed peptide is a negative antagonist of the constitutively active G protein coupled receptor, the receptor will be turned off by the exposed peptide.

In a still further embodiment for identifying peptide agonists, the expression of a peptide of a peptide library tethered to a G protein coupled receptor of interest in a cell comprises preparing a G protein coupled receptor construct, introducing the G protein coupled receptor construct into a cell, and allowing the cell to express the G protein coupled receptor encoded thereby. The G protein coupled receptor construct for identifying a peptide agonist, which is also provided by the subject invention, comprises a nucleic acid molecule encoding a G protein coupled receptor with a deleted first amino terminus; a nucleic acid molecule encoding a second amino terminus of a self-activating receptor attached to the nucleic acid molecule encoding the G protein coupled receptor at the deleted first amino terminus, the second amino terminus having a deleted portion which includes a peptide agonist for activating the self-activating receptor as well as any amino acids positioned amino terminally to the peptide agonist; and a nucleic acid molecule encoding the peptide of the peptide library inserted into the second amino terminus and replacing the deleted portion. This G protein coupled receptor construct for identifying a peptide agonist of a G protein coupled receptor has the same structure as the construct shown in FIG. 5 except that the G protein coupled receptor (10) is not a constitutively active receptor.

The Examples which follow relate to particular GPCRs, such as the human calcitonin receptor, the human follicle-stimulating hormone receptor, and a GPCR of human herpesvirus-8. However, as should be readily apparent to those of ordinary skill in the art, this invention is equally applicable to any GPCR. GPCRs are the largest family of cell surface receptors and act indirectly to regulate the activity of a separate plasma membrane-bound target protein, which can be an enzyme or an ion channel. The interaction between the receptor and the target protein is mediated by a third protein, called a trimeric GTP-binding regulatory protein (G protein). The activation of the target protein either alters the conformation of one or more intracellular mediators (if the target protein is an enzyme) or alters the ion permeability of the plasma membrane (if the target protein is an ion channel).

GPCRs include, for example, the alpha-adrenergic receptors, the beta-adrenergic receptors, dopaminergic receptors, serotonergic receptors, muscarinic cholinergic receptors, peptidergic receptors, and the thyrotropin releasing hormone receptor. GPCRs are characterized by a seven transmembrane-spanning topology (see FIGS. 1, 2, 4–8). As used herein, the amino terminus of a GPCR refers to that portion of the GPCR which is extracellular, extending from the amino end of the GPCR to the first transmembrane domain (the amino terminus is depicted in FIGS. 4 and 5).

The various G protein coupled receptor constructs of the subject invention include the amino terminus of a self-activating receptor as defined herein. In one embodiment, the self-activating receptor is the thrombin receptor. The amino acid sequence of this amino terminus of the thrombin receptor is shown in SEQ ID NO:1, with amino acid residues 9 to 13 of SEQ ID NO:1 representing the natural peptide agonist of the thrombin receptor. These residues (9 to 13 of SEQ ID NO:1) are replaced with the peptide library in accordance with the subject invention. In one embodiment of the G protein coupled receptor construct, the amino acids normally cleaved by thrombin (residues 1 to 8 of SEQ ID No:1) are also replaced by the peptide of the peptide library.

SEQ ID NO:1:
LDATLDPRSFLLRNPNDKYEPF-
WEDEEKNESGLTEYRLVSINKSSPLQK
QLPAFISEDASGYL

Figure 6:
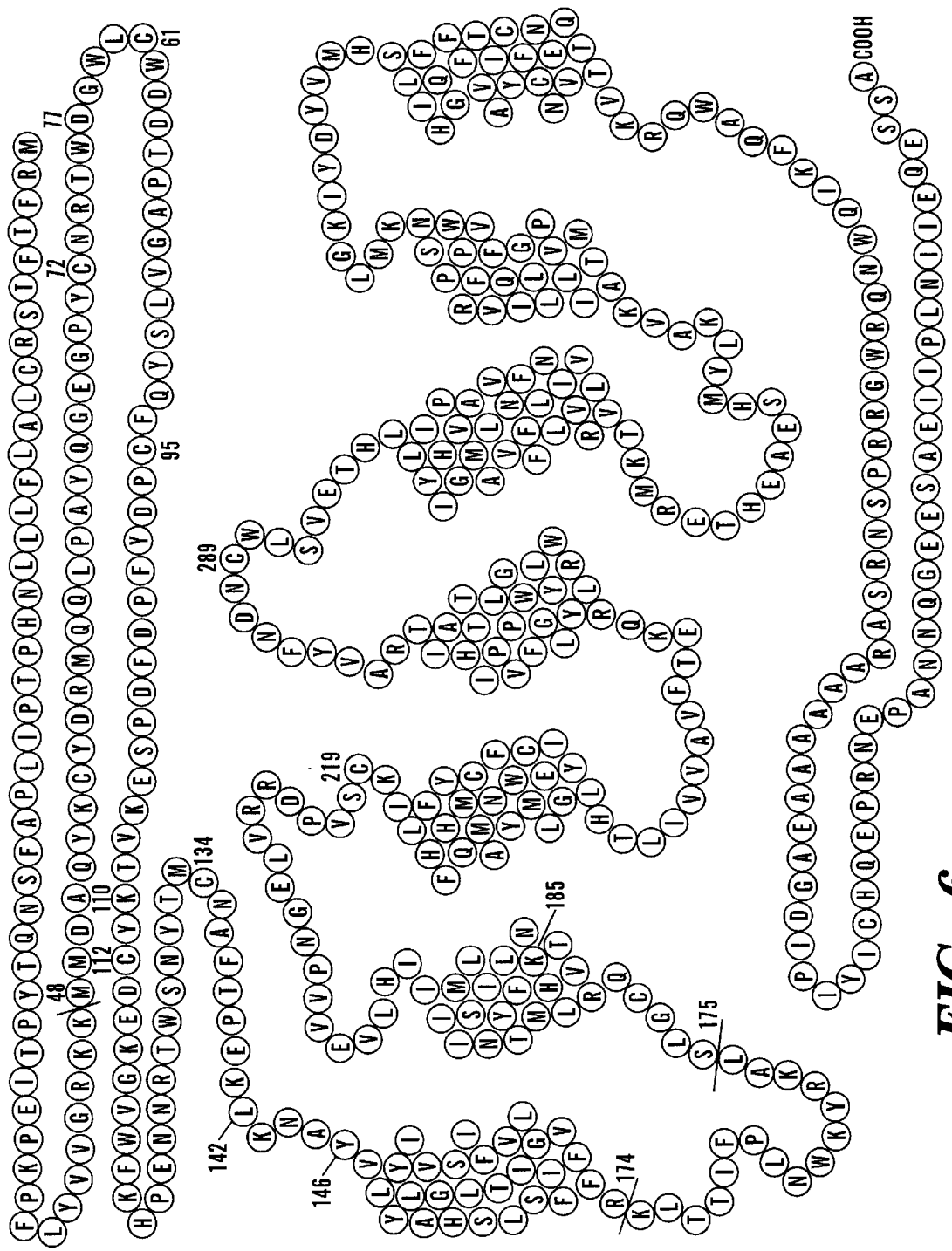
FIG. 6 is a diagram of the putative two-dimensional topology of the human calcitonin receptor.

In one embodiment discussed in the Examples, the G protein coupled receptor construct is of a human calcitonin receptor (see FIG. 6). The human calcitonin receptor construct according to the subject invention has an amino acid sequence as shown in SEQ ID NO:44, wherein amino acid residues 47 to 51 of SEQ ID NO:44 are the peptide of a peptide library, amino acid residues 1 to 101 of SEQ ID NO:44 are the second amino terminus, and amino acid residues 102 to 429 of SEQ ID NO:44 are the nucleic acid molecule encoding the human calcitonin receptor with the first amino terminus deleted.

SEQ ID NO:44:
MDSKGSSQKGSRLLLLLVVSNLLLCQGV-
VSDYKDDDDKLDATLDPRXXXXXNPNDKYEPF
WEDEEKNESGLTEYRLVSINKSS-
PLQKQLPAFISEDASGYLVLYYLAIVGH-
SLSIFTLVI SLGIFVFFRSLGCQRVTLHKNMFLTY-
ILNSMIIIHLVEVVPNGELVRRDPVSCKILHFF
HQYMMACNYFWMLCEGIYLHTLIV-
VAVFTEKQRLRWYYLLGWGFPLVPTTI-
HAITRAVYF NDNCWLSVETHLLYIIHGPV-
MAALVVNFFFLLNIVRVLVTKMRETHEAESEM
YLKAVKAT MILVPLLGIQFVVFPWRPSNKM-
LGKIYDYVMHSLIHFQGFFVATIYCFCN-
NEVQTTVKRQ WAQFKIQWNQRWGRRPSNRSA-
RAAAAAAEAGDIPIYICHQELRNEPANNQGEES
AEIIPL NIIEQESSA

In a further embodiment discussed in the Examples, the G protein coupled receptor construct is of a human follicle stimulating hormone receptor. The human follicle stimulating hormone receptor construct has an amino acid sequence as shown in SEQ ID NO:2, wherein amino acid residues 47 to 51 of SEQ ID NO:2 are the peptide of a peptide library, amino acid residues 39 to 101 of SEQ ID NO:2 are the second amino terminus, and amino acid residues 102 to 436 of SEQ ID NO:2 are the nucleic acid molecule encoding the human follicle stimulating hormone receptor with the first amino terminus deleted.

SEQ ID NO:2:
MDSKGSSQKGSRLLLLLVVSNLLLCQG-
WSDYKDDDDKLDATLDPRXXXXXNPND-
KYEPFWEDEEK NESGLTEYRLVSINKSS-
PLQKQLPAFISEDASGYLGYNILRVLIWFISILAI
TGNIIVLVILTTSQ YKLTVPRFLMCNLAFADL-
CIGIYLLLIASVDIHTKSQYHNYAID-
WQTGAGCDAGFFTVFASELSV YTLTAITLER-
WHTITHAMQLDCKVQLRHAASVMVMGWIFA
FAAALFPIFGISSYMKVSICLPMDID SPLSQLY-
VMSLLVLNVLAFWICGCYIHIYLTVRNP-
NIVSSSSDTRIAKRMAMLIFTDFLCMAPIS
FFAISASLKVPLITVSKAKILLVLFH-
PINSCANPFLYAIFTKNFRRDFFILLSKCGC YEM-
QAQIYR TETSSTVHNTHPRNGHCSSAPRVTNGS-
TYILVPLSHLAQN

As used herein, the term "as shown in" when used in conjunction with a SEQ ID NO for a nucleotide sequence refer to a nucleotide sequence which is substantially the same nucleotide sequence, or derivatives thereof (such as deletion and hybrid variants thereof, splice variants thereof, etc.). Nucleotide additions, deletions, and/or substitutions, such as those which do not affect the translation of the DNA molecule, are within the scope of a nucleotide sequence as shown in a particular nucleotide sequence (i.e. the amino acid sequence encoded thereby remains the same). Such additions, deletions, and/or substitutions can be, for example, the result of point mutations made according to methods known to those skilled in the art. It is also possible to substitute a nucleotide which alters the amino acid sequence encoded thereby, where the amino acid substituted is a conservative substitution or where amino acid homology is conserved. It is also possible to have minor nucleotide additions, deletions, and/or substitutions which do not alter the function of the resulting GPCR. These are also within the scope of a nucleotide sequence as shown a particular nucleotide sequence.

Similarly, the term "as shown in" when used in conjunction with a SEQ ID NO for an amino acid sequence refers to an amino acid sequence which is substantially the same amino acid sequence or derivatives thereof. Amino acid additions, deletions, and/or substitutions which do not negate the ability of the resulting protein (or peptide) to form a functional protein (or peptide) are within the scope of an amino acid sequence as shown in a particular amino acid sequence. Such additions, deletions, and/or substitutions can be, for example, the result of point mutations in the DNA encoding the amino acid sequence, such point mutations made according to methods known to those skilled in the art. Substitutions may be conservative substitutions of amino acids. Two amino acid residues are conservative substitutions of one another, for example, where the two residues are of the same type. In this regard, alanine, valine, leucine, isoleucine, glycine, cysteine, phenylalanine, tryptophan, methionine, and proline, all of which are nonpolar residues, are of the same type. Serine, threonine, tyrosine, asparagine, and glutamine, all of which are uncharged polar residues, are of the same type. Another type of residue is the positively charged (basic) polar amino acid residue, which includes histidine, lysine, and arginine. Aspartic acid and glutamic acid, both of which are negatively charged (acidic) polar amino acid residues, form yet another type of residue. Further descriptions of the concept of conservative substitutions are given by French and Robson 1983, Taylor 1986, and Bordo and Argos 1991.

As further used herein, the term "as shown in" when used in conjunction with a SEQ ID NO for a nucleotide or amino acid sequence is intended to cover linear or cyclic versions of the recited sequence (cyclic referring to entirely cyclic versions or versions in which only a portion of the molecule is cyclic, including, for example, a single amino acid cyclic upon itself), and is intended to cover derivative or modified nucleotide or amino acids within the recited sequence. For example, those skilled in the art will readily understand that an adenine nucleotide could be replaced with a methyladenine, or a cytosine nucleotide could be replaced with a methylcytosine, if a methyl side chain is desirable. Nucleotide sequences having a given SEQ ID NO are intended to encompass nucleotide sequences containing these and like derivative or modified nucleotides, as well as cyclic variations. As a further example, those skilled in the art will readily understand that an asparagine residue could be replaced with an ethylasparagine if an ethyl side chain is desired, a lysine residue could be replaced with a hydroxylysine if an OH side chain is desired, or a valine residue could be replaced with a methylvaline if a methyl side chain is desired. Amino acid sequences having a given SEQ ID NO are intended to encompass amino acid sequences containing these and like derivative or modified amino acids, as well as cyclic variations. Cyclic, as used herein, also refers to cyclic versions of the derivative or modified nucleotides and amino acids.

As further used herein, a nucleic acid molecule can be deoxyribonucleic acid (DNA) or ribonucleic acid (RNA), the latter including messenger RNA (mRNA). The nucleic acid can be genomic or recombinant, biologically isolated or synthetic.

The DNA molecule can be a cDNA molecule, which is a DNA copy of an mRNA encoding the protein.

The G protein coupled receptor construct of the subject invention can be expressed in suitable host cells using conventional techniques. Any suitable host and/or vector system can be used to express the GPCR construct. For in vitro expression, bacterial hosts (for example, *Escherichia coli*) and mammalian hosts (for example, COS cells) are preferred. For screening using the GPCR construct in which the inserted peptide is always exposed, yeast cells are preferred. The use of yeast cells as a host for expression of the GPCR construct allows for the screening for negative antagonists of constitutively active GPCRs or for the screening of agonists of GPCRs. Expression of the construct is desirable to identify peptide agonists and negative antagonists of the GPCR, which can then be used for study and/or research purposes, as well as for therapy of inherited or acquired human disorders related to GPCR function.

Techniques for introducing the construct into the host cells may involve the use of expression vectors which comprise the nucleic acid molecule encoding the construct. These expression vectors (such as plasmids and viruses) can then be used to introduce the nucleic acid molecule into suitable host cells. For example, DNA encoding the construct can be injected into the nucleus of a host cell or transformed into the host cell using a suitable vector, or mRNA encoding the construct can be injected directly into the host cell, in order to obtain expression of the GPCR construct in the host cell.

Various methods are known in the art for introducing nucleic acid molecules into host cells. One method is microinjection, in which DNA is injected directly into the nucleus of cells through fine glass needles (or RNA is injected directly into the cytoplasm of cells). Alternatively, DNA can be incubated with an inert carbohydrate polymer (e.g. dextran) to which a positively charged chemical group (e.g. diethylaminoethyl ("DEAE")) has been coupled. The DNA sticks to the DEAE-dextran via its negatively charged phosphate groups. These large DNA-containing particles, in turn, stick to the surfaces of cells, which are thought to take them in by a process known as endocytosis. Some of the DNA evades destruction in the cytoplasm of the cell and escapes to the nucleus, where it can be transcribed into RNA like any other gene in the cell. In another method, cells efficiently take in DNA in the form of a precipitate with calcium phosphate. In electroporation, cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures (passage through these vesicles may sometimes destroy or damage DNA). DNA can also be incorporated into artificial lipid vesicles, liposomes, which fuse with the cell membrane, delivering their contents directly into the cytoplasm. In an even more direct approach, used primarily with plant cells and tissues, DNA is absorbed to the surface of tungsten microprojectiles and fired into cells with a device resembling a shotgun.

Further methods for introducing nucleic acid molecules into cells involve the use of viral vectors. Since viral growth depends on the ability to get the viral genome into cells, viruses have devised clever and efficient methods for doing it. Various viral vectors have been used to transform mammalian cells, such as vaccinia virus, adenovirus, and retrovirus.

As indicated, some of these methods of transforming a cell require the use of an intermediate plasmid vector. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook et al. (1989).

Host cells into which the nucleic acid encoding the construct has been introduced can be used to produce (i.e. to functionally express) the GPCR construct. The cell can then be monitored to determine whether the peptide tethered to the GPCR is an agonist or negative antagonist (in the case of a constitutively active GPCR) of the GPCR. The method of monitoring can be chosen based on the signalling pathway of the GPCR, or the construct can further include marker or reporter systems as discussed in further detail below. For example, if the G protein coupled receptor signals through an ion channel pathway, the monitoring can comprise detecting levels of the ion within the cell. If the G protein coupled receptor signals through a calcium ion channel pathway, the cell to be used can be a Xenopus oocyte and the monitoring can comprise voltage clamp analysis. If the G protein coupled receptor signals through a cyclic adenosine monophosphate pathway, the monitoring can comprise detecting levels of cyclic adenosine monophosphate within the cell.

The invention further provides a cell comprising the G protein coupled receptor construct of the subject invention, as well as an expression vector comprising the construct. A host cell comprising the expression vector is also provided. Such expression vectors include a plasmid and a virus. Preferably, the cell into which the construct or expression vector (comprising the construct) is introduced is a Xenopus oocyte, a mammalian cell (such as COS-1 cells; see Gershengorn and Osman 1996), or a yeast cell.

EXAMPLE I

Peptide Agonists of hFSH-R

A combinatorial peptide library was constructed that expresses random pentapeptides tethered to the seven transmembrane helical bundle of the human follicle-stimulating hormone receptor (hFSH-R). This library encompasses all 20 natural amino acids at each of the five positions, and, therefore, has a complexity of $20^5=3.2 \times 10^6$ possible combinations. To this end, the complementary DNA sequence that normally encodes the hFSH-R's amino terminal extracellular domain was substituted by a DNA sequence that encodes the thrombin receptor's amino terminal ectodomain. The chimeric human THR-R/FSH-R has the variable pentapeptide sequence substituting for the native peptide sequence that is normally unmasked by thrombin action and constitutes the thrombin receptor agonist peptide, but it retains thrombin binding sequences and the thrombin specific cleavage site. Therefore, the amino terminus of expressed receptors is cleavable by thrombin at the appropriate location exposing a new amino terminus that is made of the variable pentapeptide segment of the library tethered to the transmembrane domains of hFSH-R.

To monitor for cell surface expression and efficient cleavage by thrombin of the amino terminal end of the chimeric receptors, an epitope-tag to which antibodies are available was positioned proximally to the thrombin cleavage site. Antibodies that recognize thrombin receptor amino terminus distal to the position corresponding to the library are also available. Consequently, chimeric receptors expressed on the cell surface are detectable by the appropriate use of both types of specific antibodies before thrombin treatment, but only with antibodies against the distal part after thrombin treatment.

The amino acid sequence of the chimeric human THR-R/FSH-R is shown in SEQ ID NO:2:

MDSKGSSQKGSRLLLLLVVSNLLLCQG-WSDYKDDDDKLDATLDPRXXXXXNPND-KYEPFWEDEEK NESGLTEYRLVSINKSS-PLQKQLPAFISEDASGYLGYNILRVLIWFISILAI TGNIIVLVILTTSQ YKLTVPRFLMCNLAFADL-CIGIYLLLIASVDIHTKSQYHNYAID-WQTGAGCDAAGFFTVFASELSV YTLTAITLER-WHTITHAMQLDCKVQLRHAASVMVMGWIFA FAAALFPIFGISSYMKVSICLPMDID SPLSQLY-VMSLLVLNVLAFVVICGCYIHIYLTVRN-PNIVSSSSDTRIAKRMAMLIFTDFLCMAPIS FFAISASLKVPLITVSKAKILLVLFH-PINSCANPFLYAIFTKNFRRDFFILLSKCGC YEM-QAQIYR TETSSTVHNTHPRNGHCSSAPRVTNGS-TYILVPLSHLAQN

The construct consists of 436 amino acids: amino acid residues 1–30 represent the prolactin signal peptide (SEQ ID NO:6: MDSKGSSQKGSRLLLLLVVSNLLLCQGVVS); residues 31–38 represent the FLAG epitope (SEQ ID NO:4: DYKDDDDK); residues 39–101 represent amino acids from the hTHR receptor of which residues 47–51 represent the pentapeptide (SEQ ID NO:5: XXXXX) and residues 57–74 represent the hirudin epitope; and residues 102–436 represent amino acids from the hFSH receptor of which residues 108–128 represent transmembrane domain 1, residues 140–162 represent transmembrane domain 2, residues 185–206 represent transmembrane domain 3, residues 227–250 represent transmembrane domain 4, residues 270–291 represent transmembrane domain 5, residues 316–338 represent transmembrane domain 6, and residues 350–371 represent transmembrane domain 7. The signal peptide cleavage site lies between amino acid residues 30 and 31 of SEQ ID NO:2, and the thrombin cleavage site lies between amino acid residues 46 and 47 of SEQ ID NO:2. Cleavage with thrombin thus exposes the pentapeptide that is amino acid residues 47–51 of SEQ ID NO:2.

The construction of the DNA sequence encoding the amino acid sequence shown in SEQ ID NO:2 took several steps that are described below:

1) Construction of a sequence encoding the prolactin signal peptide (SEQ ID NO:3) followed by a FLAG epitope-tag (SEQ ID NO:4: DYKDDDDK) placed immediately upstream of the putative mature sequence for human thrombin receptor amino terminus ectodomain (from amino acids 34 to 96, SEQ ID NO:1) was produced by gene synthesis using standard techniques as described (Nussenzveig 1994). Synthetic oligonucleotides obtained for the prolactin leader sequence-FLAG epitope-tag construction have the following sequences: coding strand PROLAC-1: SEQ ID NO:6: 5'-AAT TCC ACC ATG GAC TCC AAG GGC TCG AGC CAG AAG GGA TCT AGA CTG CT-3'; complementary strand PROLAC-2: SEQ ID NO:7: 5'-$PO_4$-CAG CAG CAG TCT AGA TCC CTT CTG GCT CGA GCC CTT GGA GTC CAT GGT GG-3'; coding strand PROLAC-3: SEQ ID NO:8: 5'-$PO_4$-G CTG CTG CTG GTG GTG AGC AAC CTG CTG CTG TGC CAG GGC GTC GTG-3; complementary strand PROLAC-4: SEQ ID NO:9: 5'-$PO_4$-CGC TCA CGA CGC CCT GGC ACA GCA GCA GGT TGC TCA CCA CCA GCA G-3'; FLAG-SENSE: SEQ ID NO:10: 5'-$PO_4$-AGC GAC TAC AAG GAC GAC GAC GAC AAG CTT CCT GCC TTT T-3'; FLAG-ANTI-SENSE: SEQ ID NO:11: 5'-CGA AAA GGC AGG AAG CTT GTC GTC GTC GTC CTT GTA GT-3'. The pair of oligonucleotides PROLAC-1/PROLAC-2; PROLAC-3/PROLAC-4; and FLAG-SENSE/FLAG-ANTI-SENSE were annealed separately at 20 μM final oligonucleotide concentration, by heating at 95° C. for 5 min and cooling to 4° C. at a rate of 1° C. every 3 min, in 20 mM Tris-Cl pH 7.6 and 10 mM $MgCl_2$ buffer, using a thermal controller apparatus. Double stranded DNA was purified by agarose gel electrophoresis using the Mermaid™ purification system (Bio 101). Purified double stranded oligonucleotides were ligated using equal molar concentrations. Ligation products were digested with HindIII after heat inactivation of T4 DNA ligase. The resulting 125 bp larger fragment was purified by agarose gel electrophoresis using the Mermaid™ kit. Fragment of interest was subcloned into EcoRI and HindIII sites of pBSSKII(+). Correctness of the sequence was verified by dideoxynucleotide sequencing method using Circumvent sequencing kit (New England Biolabs, Inc.).

2) Construction of a sequence encoding the human thrombin receptor amino terminus from amino acid residue $F^{55}$ to $L^{96}$ (residues 60–101 of SEQ ID NO:2) was obtained by assembling four synthetic overlapping oligonucleotides containing gaps from 10 to 33 nucleotides: coding strand THRR-1: SEQ ID NO:12: 5'-TAT GCC ACC TTT TGG GAG GAT GAG GAG AAA AAT GAA AGT GGG TTA ACT GAA TAC-3'; complementary strand THRR-2: SEQ ID NO:13: 5'-TG AAG AGG ACT GCT TTT ATT GAT GGA GAC TAA TCT GTA TTC AGT TAA CCC ACT TTC-3'; coding strand THRR-3: SEQ ID NO:14: 5'-C AAT AAA AGC AGT CCT CTT CAA AAA CAA CTT CCT GCA TTC ATC TCA GAA GAT GCC-3'; complementary strand THRR BstEII:SEQ ID NO:15: 5'-GT CAG GTA ACC GGA GGC ATC TTC TGA GAT GAA TGC AAG-3'. Oligonucleotide THRR BstEII inadvertently mutated hTHRR codon for p$^{85}$ into L. Oligonucleotides THRR-2 and THRR-3 were phosphorylated enzymaticaly using T4 polynucleotide kinase in 50 mM Tris-HCl pH 7.5, 10 mM MgCl$_2$, 10 mM dithiothreitol, 1 mM ATP and 25 µg/ml BSA. Oligonucleotides THRR-1, THRR-2, THRR-3 and THRR BstEII were annealed at a final concentration of 10 µM in 20 mM Tris-Cl pH 7.6, 10 mM MgCl$_2$ buffer by heating at 95° C. for 5 min and cooling to 4° C. at a rate of 1° C. per 8 min using a thermal controller apparatus. The gaps between annealed oligonucleotides were filled-in using T4 DNA polymerase. Reaction was performed at a final concentration of 2.5 µM oligonucleotides, 400 µM dNTPs, 50 mM NaCl, 15 mM Tris-HCl, 12.5 mM MgCl$_2$, 1 mM dithiothreitol, 50 µg/ml BSA, pH 7.9 at 25° C. for 60 min. Reaction was stopped with 25 mM EDTA and enzyme was heat inactivated at 65° C. for 60 min. T4 DNA polymerase was selected not only to avoid strand displacement of the overlapping oligonucleotides but also because of its 3' to 5' exonuclease activity to correct the inadvertent mutation p$^{85}$ to L.

3) Construction of a nucleotide sequence encoding amino acid residues from G$^{361}$ to N$^{694}$ (residues 102–436 of SEQ ID NO:2) followed by the stop codon of the hFSHR was obtained by standard taq polymerase PCR method using the following pair of oligonucleotides: i) coding strand FSHR BStEII: SEQ ID NO:16: 5'-T GAA GGT TAC CTG GGG TAC AAC ATC CTC AGA GTC C-3'; and ii) complementary strand NotI 2170: SEQ ID NO:17: 5'-TCA CGC GGC CGC TTA GTT TTG GGC TAA ATG ACT TAG AGG-3'. The resultant PCR product creates BstEII and NotI sites at the 5' and 3' ends of the coding strand, respectively. The BstEII site was used to connect the hFSHR sequence in frame with the amino terminus ectodomain of the hTHRR. The NotI site was used to connect the chimeric construct to the expression vector. Resulting PCR product was cloned into a pBSSKII(+)AT vector prepared to receive PCR fragments containing non-template dependent addition of 3' A-overhangs. pBSSKII(+)AT vector, that contains 3' T-overhangs, was obtained by ligating phosphorylated oligonucleotides AT-SENSE: SEQ ID NO:18: 5'-PO$_4$-AAT TCG GCT T-3' and AT-ANTI-SENSE: SEQ ID NO:19: 5'-PO$_4$-AGC CG-3' into pBSSKII(+) vector cut with EcoRI. A clone was selected with the orientation that places the newly created BstEII site closer to the SacI site of the vector and the NotI site of the insert closer to the KpnI site of the vector.

4) Modification of the hFSHR construct obtained in item # 3 through the production of silent mutations to destroy the two PflMI sites originally present at positions 1,379 and 2,080 of the hFSHR cDNA. hFSHR DNA sequence was modified by PCR mutagenesis, using the construct obtained in item # 3 as a template in a standard PCR reaction with tag polymerase and the following three pairs of primers: i) PvuI 1379—ANTI-SENSE: SEQ ID NO:20: 5'-CA GTC GAT CGC ATA GTT GTG ATA TTG GCT C-3' and vector REVERSE PRIMER: SEQ ID NO:21: 5'-AAC AGC TAT GAC CAT G-3'. This PCR fragment contains a silent mutation that at the same time destroys a PflMI site present at position 1379 of the human FSHR cDNA and introduces a PvuI site at the same position. ii) SacII 2080—SENSE: SEQ ID NO:22: 5'-C CAT CCG CGG AAT GGC CAC TGC TCT TCA GC-3' and vector M13 (–20) PRIMER: SEQ ID NO:23: 5'-GTA AAA CGA CGG CCA GT-3'. This PCR fragment contains a silent mutation that at the same time destroys a PflMI site present at position 2,080 of the human FSHR CDNA and introduces a SacII site at the same position. iii) PvuI 1379—SENSE: SEQ ID NO:24: 5'-TAT GCG ATC GAC TGG CAA ACT GGG GCA GG-3' and SacII 2080—ANTI-SENSE: SEQ ID NO:25: 5'-C ATT CCG CGG ATG GGT GTT GTG GAC AGT G-3'. PCR fragment that contains two silent mutations that simultaneously change a PflMI site present at positions 1,379 into a PvuI site and a PflMI site present at position 2,080 into a SacII site (numbers refer to the nucleotide sequence of the original hFSHR cDNA). PCR fragments originated with oligonucleotide pairs: i) was cut with the restriction enzymes BstEII and PvuI and a 225 bp DNA fragment was purified by agarose gel electrophoresis followed by the GeneClean™ procedure; ii) was cut with the restriction enzymes SacII and ApaI and a 700 bp DNA fragment was purified by agarose gel electrophoresis followed by the GeneClean™ procedure; iii) was cut with the restriction enzymes PvuI and SacII and a 140 bp DNA fragment was purified by agarose gel electrophoresis followed by the Mermaid™ procedure. Construct obtained in step # 3 was cut with the restriction enzymes BstEII and ApaI and a 2.9 kbp DNA fragment was purified by agarose gel electrophoresis followed by the GeneClean™ procedure. Finally the four purified DNA fragments were ligated together to produce a modified hFSHR construct in pBSSKII(+)AT vector.

5) Assembling of the hTHRR amino terminus ectodomain obtained from step # 2 with the modified hFSHR construct obtained from step # 4: the DNA fragment encoding the hTHRR amino terminus from amino acid residue F$^{55}$ to L$^{96}$ obtained from step # 2 was digested with the restriction enzyme BstEII; the modified pBSSKII(+)AT-hFSHR construct obtained from step # 4 was linearized with the restriction enzyme SacI and blunted with T4 DNA polymerase to remove 3' overhangs. After enzyme inactivation, blunted linear pBSSKII(+)AT-hFSHR was cut with the restriction enzyme BstEII. After appropriate DNA fragment purification the two modified DNA fragments (hTHRR Blunt-BstEII ~130 bp long and pBSSKII(+)AT-hFSHR Blunt-BstEII ~3,800 bp long) generated at this step (# 5) were ligated together to form the intermediate construct pBSSKII(+)hTHRR/hFSHR. Correctness of the sequence was verified by dideoxynucleotide sequencing method using Circumvent sequencing kit (New England Biolabs, Inc.).

6) Plasmid construct generated at step # 1 (pBSSKII(+) PROLAC FLAG (EcoRI-HindIII)) was cut with the restriction enzymes HindIII and ApaI and the larger fragment was purified by the GeneClean™ procedure. Plasmid construct obtained at step # 6 (intermediate pBSSKII(+)hTHRR/ hFSHR) was cut with the restriction enzymes PflMI and ApaI and the resulting ~1,100 bp DNA fragment was purified by agarose gel electrophoresis followed by the GeneClean™ procedure. A pair of oligonucleotides CONNECT-SENSE: SEQ ID NO:26: 5'-AG CTT GAT GCC ACG CTA TGG CCC TAG GTA AGT GAT ATG CCA CCT T-3'; and CONNECT-ANTI-SENSE: SEQ ID NO:27: 5'-G TGG CAT ATC ACT TAC CTA GGG CCA TAG CGT GGC ATC A-3' were annealed and purified using the procedure described in step # 1. Annealed CONNECT-SENSE/ CONNECT-ANTI-SENSE oligonucleotides were used to adapt the overhang created by HindIII digestion of pBSSKII (+) PROLAC FLAG with the overhang created by PflMI digestion of intermediate pBSSKII(+)hTHRR/hFSHR, both mentioned above. Therefore, a ligation of the two DNA fragments purified above was performed using the adaptor CONNECT-SENSE/CONNECT-ANTI-SENSE. This adaptor not only regenerates the two restriction enzyme sites, HindIII and PflMI, but also introduces a second PflMI site between the HindIII and the first PflMI sites. PflMI restriction enzyme recognition sequence is an interrupted palindrome that allows for the directional clone of DNA fragments with appropriate overhangs. The two PflMI restriction enzyme sites were created to subclone a synthetic DNA fragment that introduces, in frame with both the prolactin leader sequence/FLAG epitope tag and the chimeric hTHRR/hFSHR sequence described in step # 5, the variable pentapeptide agonist library preceded and followed by hTHRR amino acid residues corresponding to hTHRR residues from $L^{34}$ to $P^{55}$. CONNECT-SENSE/CONNECT-ANTI-SENSE adaptor sequence introduces stop codons at each of the three possible reading frames to decrease background levels during the construction of the library. Correctness of the sequence was verified by dideoxynucleotide sequencing method using automatic sequencing.

Figure 9:
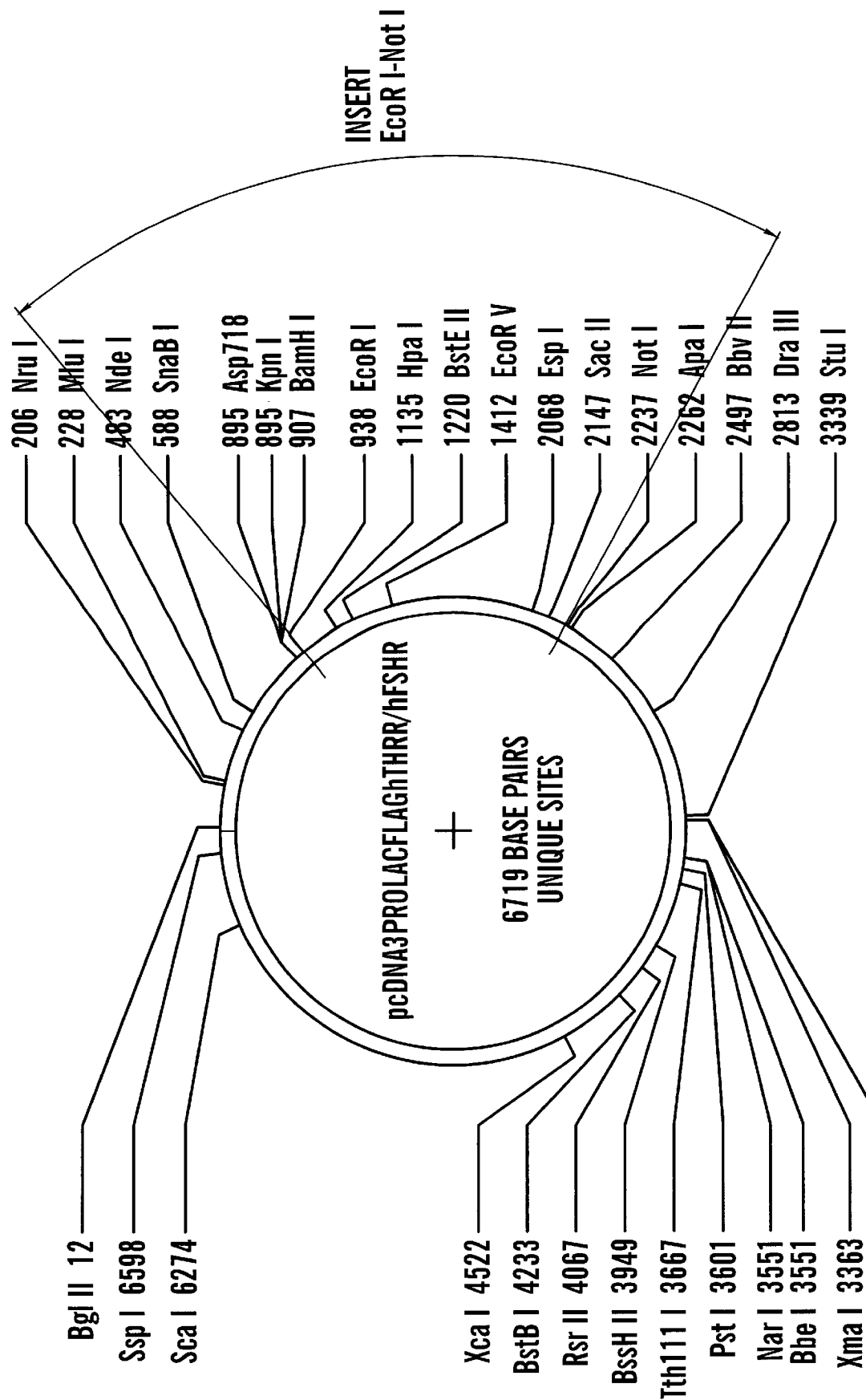
FIG. 9 is a plasmid map of pcDNA3PROLACFLAGhTHRR/hFSHR.

7) Subcloning of the construct obtained at step 6 into the mammalian expression vector pcDNA3 and into unmodified pBSSKII(+). Plasmid obtained in step # 6 was digested with EcoRI and NotI, followed by purification of the ~1300 bp DNA insert. pcDNA3 and pBSSKII(+) were both prepared by cutting with EcoRI and NotI. Insert and vectors were ligated. A library created in the vector pcDNA3 is used in transfection experiments using mammalian cells. FIG. 9 shows the plasmid map for the THRR/FSHR construct designated pcDNA3PROLACFLAGhTHRR/hFSHR. A library created in the vector pBSSKII(+) is used for in vitro transcription after linearization with the restriction enzyme NotI. Resulting RNAs are injected into Xenopus oocytes.

8) Library construction: three oligonucleotides: coding strand LIBRARY-1: SEQ ID NO:28: 5'-$PO_4$-A GAT CCC CGG NNS NNS NNS NNS NNS AAC CCC AAT GAT AAA TAT GAA CCC TT-3', where N means all four nucleotides and S means either G or C, a degenerate oligonucleotide pool with 225 different nucleic acid molecules, encoding $20^5$ different pentapeptide sequences; complementary strand LIBRARY-2: SEQ ID NO:29: 5'-$PO_4$-CCG GGG ATC TAG C-3'; and complementary strand LIBRARY-3: SEQ ID NO:30: 5'-$PO_4$-GG TTC ATA TTT ATC-3' were annealed at a molar ratio of 1 (LIBRARY-1): 25 (LIBRARY-2): 25 (LIBRARY-3) in 20 mM Tris-HCl pH 7.6 , 10 mM $MgCl_2$, by heating at 95° C. for 5 min and cooling to 4° C. at a rate of 1° C. per 8 min using a thermal controller apparatus. Annealed oligonucleotides were purified by agarose gel electrophoresis using the Mermaid™ kit. pcDNA3 PROLACFLAG-CONNECT-SENSE/CONNECT-ANTI-SENSE-hTHRR/hFSHR or pBSSKII(+) PROLACFLAG-CONNECT-SENSE/CONNECT-ANTI-SENSE-hTHRR/hFSHR from step # 7 were cut with the restriction enzyme PflMI to completion. Purified large fragment of each construct was ligated with the annealed library oligonucleotides at approximately 1:3 molar ratios. The ligated products were ethanol precipitated and redissolved in water for transformation of *E. coli* XL1-Blue cells by electroporation.

Shown below is the nucleotide sequences of PROLAC FLAG—CONNECT-SENSE/CONNECT- ANTI-SENSE—hTHRR/hFSHR and of the assembled LIBRARY-1, -2 and -3 oligonucleotides to be ligated into the two PflMI sites of the insert, substituting for most of the sequence corresponding to CONNECT-SENSE/CONNECT-ANTI-SENSE:

```
Eco R I AATTCCACC ATG GAC TCC AAG GGC TCG AGC CAG AAG
                 GGTGG TAC CTG AGG TTC CCG AGC TCG GTC TTC
                       M   D   S   K   G   S   S   Q   K

GGA TCT AGA CTG CTG CTG CTG CTG GTG GTG AGC AAC CTG CTG
CCT AGA TCT GAC GAC GAC GAC GAC CAC CAC TCG TTG GAC GAC
 G   S   R   L   L   L   L   L   V   V   S   N   L   L

CTG TGC CAG GGC GTC GTG AGC GAC TAC AAG GAC GAC GAC GAC
GAC ACG GTC CCG CAG CAC TCG CTG ATG TTC CTG CTG CTG CTG
 L   C   Q   G   V   V   S   D   Y   K   D   D   D   D

A Hind III AG CTT GAT GCC ACG CT Pfl M I A TGG CCC TAG
TTC GA         A CTA CGG TG         C GAT ACC GGG ATC
            K  L   D   A   T   L                    *

GTA AGT GAT ATG CCAC C TT Pfl M I T TGG GAG GAT GAG GAG
CAT TCA CTA TAC GG           G AAA ACC CTC CTA CTC CTC
 *   *                         F   W   E   D   E   E

AAA AAT GAA AGT GGG TTA ACT GAA TAC AGA TTA GTC TCC ATC
TTT TTA CTT TCA CCC AAT TGA CTT ATG TCA AAT CAG AGG TAG
 K   N   E   S   G   L   T   E   Y   R   L   V   S   I

AAT AAA AGC AGT CCT CTT CAA AAA CAA CTT CCT GCA TTC ATC
TTA TTT TCG TCA GGA GAA GTT TTT GTT GAA GGA CGT AAG TAG
 N   K   S   S   P   L   Q   K   Q   L   P   A   F   I

TCA GAA GAT GCC TCC G Bst E II GT TAC CTG GGG TAC AAC
AGT CTT CTA CGG AGG   CCA ATG              GAC CCC ATG TTG
 S   E   D   A   S           G   Y   L   G   Y   N

ATC CTC AGA GTC CTG ATA TGG TTT ATC AGC ATC CTG GCC ATC
TAG GAG TCT CAG GAC TAT ACC AAA TAG TCG TAG GAC CGG TAG
 I   L   R   V   L   I   W   F   I   S   I   L   A   I

ACT GGG AAC ATC ATA GTG CTA GTG ATC CTA ACT ACC AGC CAA
TGA CCC TTG TAG TAT CAC GAT CAC TAG GAT TGA TGG TCG GTT
 T   G   N   I   I   V   L   V   I   L   T   T   S   Q

TAT AAA CTC ACA GTC CCC AGG TTC CTT ATG TGC AAC CTG GCC
```

```
                     -continued
ATA TTT GAG TGT CAG GGG TCC AAG GAA TAC ACG TTG GAC CGG
 Y   K   L   T   V   P   R   F   L   M   C   N   L   A TTT GCT GAT CTC TGC ATT GGA ATC TAC CTG CTG CTC ATT GCA
AAA CGA CTA GAG ACG TAA CCT TAG ATG GAC GAC GAG TAA CGT
 F   A   D   L   C   I   G   I   Y   L   L   L   I   A TCA GTT GAT ATC CAT ACC AAG AGC CAA TAT CAC AAC TAT GCG
AGT CAA CTA TAG GTA TGG TTC TCG GTT ATA GTG TTG ATA CGC
 S   V   D   I   H   T   K   S   Q   Y   H   N   Y   A AT PvuI C GAC TGG CAA ACT GGG GCA GGC TGT GAT GCT GCT
       TAG CTG ACC GTT TGA CCC CGT CCG ACA CTA CGA CGA
 I        D   W   Q   T   G   A   G   C   D   A   A GGC TTT TTC ACT GTC TTT GCC AGT GAG CTG TCA GTC TAC ACT
CCG AAA AAG TGA CAG AAA CGG TCA CTC GAC AGT CAG ATG TGA
 G   F   F   T   V   F   A   S   E   L   S   V   Y   T CTG ACA GCT ATC ACC TTG GAA AGA TGG CAT ACC ATC ACG CAT
GAC TGT CGA TAG TGG AAC CTT TCT ACC GTA TGG TAG TGC GTA
 L   T   A   I   T   L   E   R   W   H   T   I   T   H GCC ATG CAG CTG GAC TGC AAG GTG CAG CTC CGC CAT GCT GCC
CGG TAC GTC GAC CTG ACG TTC CAC GTC GAG GCG GTA CGA CGG
 A   M   Q   L   D   C   K   V   Q   L   R   H   A   A AGT GTC ATG GTG ATG GGC TGG ATT TTT GCT TTT GCA GCT GCC
TCA CAG TAC CAC TAC CCG ACC TAA AAA CGA AAA CGT CGA CGG
 S   V   M   V   M   G   W   I   F   A   F   A   A   A CTC TTT CCC ATC TTT GGC ATC AGC AGC TAC ATG AAG GTG AGC
GAG AAA GGG TAG AAA CCG TAG TCG TCG ATG TAC TTC CAC TCG
 L   F   P   I   F   G   I   S   S   Y   M   K   V   S ATC TGC CTG CCC ATG GAT ATT GAC AGC CCT TTG TCA CAG CTG
TAG ACG GAC GGG TAC CTA TAA CTG TCG GGA AAC AGT GTC GAC
 I   C   L   P   M   D   I   D   S   P   L   S   Q   L TAT GTC ATG TCC CTC CTT GTG CTC AAT GTC CTG GCC TTT GTG
ATA CAG TAC AGG GAG GAA CAC GAG TTA CAG GAC CGG AAA CAC
 Y   V   M   S   L   L   V   L   N   V   L   A   F   V GTC ATC TGT GGC TGC TAT ATC CAC ATC TAC CTC ACA GTG CGG
CAG TAG ACA CCG ACG ATA TAG GTG TAG ATG GAG TGT CAC GCC
 V   I   C   G   C   Y   I   H   I   Y   L   T   V   R AAC CCC AAC ATC GTG TCC TCC TCT AGT GAC ACC AGG ATC GCC
TTG GGG TTG TAG CAC AGG AGG AGA TCA CTG TGG TCC TAG CGG
 N   P   N   I   V   S   S   S   D   T   R   I   A AAG CGC ATG GCC ATG CTC ATC TTC ACT GAC TTC CTC TGC ATG
TTC GCG TAC CGG TAC GAG TAG AAG TGA CTG AAG GAG ACG TAC
 K   R   M   A   M   L   I   F   T   D   F   L   C   M GCA CCC ATT TCT TTC TTT GCC ATT TCT GCC TCC CTC AAG GTG
CGT GGG TAA AGA AAG AAA CGG TAA AGA CGG AGG GAG TTC CAC
 A   P   I   S   F   F   A   I   S   A   S   L   K   V CCC CTC ATC ACT GTG TCC AAA GCA AAG ATT CTG CTG GTT CTG
GGG GAG TAG TGA CAC AGG TTT CGT TTC TAA GAC GAC CAA GAC
 P   L   I   T   V   S   K   A   K   I   L   L   V   L TTT CAC CCC ATC AAC TCC TGT GCC AAC CCC TTC CTC TAT GCC
AAA GTG GGG TAG TTG AGG ACA CGG TTG GGG AAG GAG ATA CGG
 F   H   P   I   N   S   C   A   N   P   F   L   Y   A ATC TTT ACC AAA AAC TTT CGC AGA GAT TTC TTC ATT CTG CTG
TAG AAA TGG TTT TTG AAA GCG TCT CTA AAG AAG TAA GAC GAC
 I   F   T   K   N   F   R   R   D   F   F   I   L   L AGC AAG TGT GGC TGC TAT GAA ATG CAA GCC CAA ATT TAT AGG
TCG TTC ACA CCG ACG ATA CTT TAC GTT CGG GTT TAA ATA TCC
 S   K   C   G   C   Y   E   M   Q   A   Q   I   Y   R ACA GAA ACT TCA TCC ACT GTC CAC AAC ACC CAT CCG C Sac
TGT CTT TGA AGT AGG TGA CAG GTG TTG TGG GTA GG
 T   E   T   S   S   T   V   H   N   T   H   P

II GG AAT GGC CAC TGC TCT TCA GCT CCC AGA GTC ACC AAT
```

-continued
```
C GCC TTA CCG GTG ACG AGA AGT CGA GGG TCT CAG TGG TTA
  R   N   G   H   C   S   S   A   P   R   V   T   W GGT TCC ACT TAC ATA CTT GTC CCT CTA AGT CAT TTA GCC CAA
CCA AGG TGA ATG TAT GAA CAG GGA GAT TCA GTA AAT CGG GTT
 G   S   T   Y   I   L   V   P   L   S   H   L   A   Q AAC TAA GC Not I
TTG ATT CGCCGG
 N   *
```

The DNA sequence (sense strand) is shown in SEQ ID NO:31, with the antisense strand shown in SEQ ID NO:32. The DNA sequence is the sequence that would encode the amino acid sequence (SEQ ID NO:33) of the chimeric preprotein that is prolactin signal peptide/FLAG epitope tag/hTHR receptor amino terminus corresponding to amino acid residues 34 to 96 in the native receptor/hFSH receptor. There are three nonsense ("stop") codons (one in each potential reading frame) in the middle of the sequence encoding the hTHR receptor amino terminus that are present to prevent translation of this precursor sequence if this sequence persisted, that is remained uncut, during construction of the final library (see below). These "stop" codons, therefore, would prevent translation of non-recombinant protein. To construct the library, this sequence (SEQ ID NO:31) is cut with PflMI to excise one small DNA fragment flanked by two PflMI restriction sites that is replaced with the following DNA sequences: sense, SEQ ID NO:28; antisense, SEQ ID NO:29 and SEQ ID NO:30) that encodes the pentapeptide library (amino acid SEQ ID NO:42):

```
Pfl M I A GAT CCC CGG NNS NNS NNS NNS NNS AAC CCC AAT
        C GAT CTA GGG GCC
 T   L   D   P   R   X   X   X   X   X   N   P   N

GAT AAA TAT GAA CCC TT Pfl M I
CTA TTT ATA CTT GG
 D   K   Y   E   P   F
```

Modification of the original construct with the intent to create a combinatorial peptide library that expresses random pentapeptides tethered to the seven transmembrane helical bundle of any GPCR already in an "active" or "exposed" form, without the need for cleavage by thrombin. Use of the human follicle stimulating hormone receptor (hFSH-R) as the initial library construction:

In this version of the library, the variable pentapeptide sequence is placed immediately after the prolactin signal peptide. Consequently, the cleavage produced by the signal peptidase that normally occurs during synthesis of type III membrane proteins would expose or "activate" the pentapeptide present at the beginning of the amino terminus, allowing it to interact with the seven transmembrane helical bundle of the GPCR to which it is tethered. The resulting protein sequence of the amino terminus ectodomain that can replace the amino terminus ectodomain of any GPCR is shown in SEQ ID NO:34:

MDSKGS SQKGSRLLLLLVVSNLLLCQGV-
VSXXXXXNPNDKYEPFWEDEEKNES-
GLTEYRLVS INKS SPLQKQLPAFISEDASGYL

To create this construct it is necessary to perform a small modification in the construct already obtained for the discovery of peptide agonists for the hFSHR using thrombin activation. By silent mutation using PCR method, it is possible to introduce a new PflMI restriction endonuclease cleavage site in the sequence of prolactin signal peptide construct obtained previously at step # 1: PCR using the pair of oligonucleotide primers:complementary strand PflMI SIGNAL: SEQ ID NO:35: 5'-ATC AAG CTT GTC GTC GTC GTC CTT GTA GTC GCT CAC CAC GCC CTG-3' and vector M13 (−20) PRIMER: SEQ ID NO:23: 5'-GTA AAA CGA CGG CCA GT-3', using as template the construct pBSSKII(+) PROLAC FLAG—CONNECT-SENSE/CONNECT-ANTI-SENSE—hTHRR/hFSHR. Resulting PCR product is cut with EcoRI and HindIII. This fragment will substitute the corresponding fragment in pBSSKII(+) PROLAC FLAG—CONNECT-SENSE/CONNECT-ANTI-SENSE—hTHRR/hFSHR, therefore introducing a third PflMI restriction enzyme recognition site at the desired position. See sequence below (sense, SEQ ID NO:36; antisense, SEQ ID NO:37; amino acid, SEQ ID NO:38):

```
Eco R I AATTCCACC ATG GAC TCC AAG GGC TCG AGC CAG AAG
            GGTGG TAC CTG AGG TTC CCG AGC TCG GTC TTC
                   M   D   S   K   G   S   S   Q   K
```

```
GGA TCT AGA CTG CTG CTG CTG CTG GTG GTG AGC AAC CTG CTG
CCT AGA TCT GAC GAC GAC GAC GAC CAC CAC TCG TTG GAC GAC
 G   S   R   L   L   L   L   L   V   V   S   N   L   L

CTG TGC CAG GGC Pfl M I GTG GTG AGC GAC TAC AAG GAC GAC GAC
GAC ACG GTC             CCG CAC CAC TCG CTG ATG TTC CTG CTG
 L   C   Q   G           V   V   S   D   Y   K   D   D

GAC GAC A Hind III AG CTT GAT GCC ACG CT Pfl M I  A TGG
CTG CTG TTC GA        A CTA CGG TG             C GAT ACC
 D   D         K   L   D   A   T   L              L   W CCC TAG GTA AGT GAT ATG CCAC C TT Pfl M I   T TGG GAG GAT
GGG ATC CAT TCA CTA TAC GGTG            G AAA ACC CTC CTA
 P   *   *   *                            F   W   E   D GAG GAG AAA AAT GAA AGT GGG TTA ACT GAA TAC AGA TTA GTC TCC
CTC CTC TTT TTA CTT TCA CCC AAT TGA CTT ATG TCA AAT CAG AGG
 E   E   K   N   E   S   G   L   T   E   Y   R   L   V   S ATC AAT AAA AGC AGT CCT CTT CAA AAA CAA CTT CCT GCA TTC ATC
TAG TTA TTT TCG TCA GGA GAA GTT TTT GTT GAA GGA CGT AAG TAG
 I   N   K   S   S   P   L   Q   K   Q   L   P   A   F   I TCA GAA GAT GCC TCC G Bst E II GT TAC CTG GGG TAC AAC
AGT CTT CTA CGG AGG   CCA ATG      GAC CCC ATG TTG
 S   E   D   A   S             G   Y   L   G   Y   N ATC CTC AGA GTC CTG ATA TGG TTT ATC AGC ATC CTG GCC ATC
TAG GAG TCT CAG GAC TAT ACC AAA TAG TCG TAG GAC CGG TAG
 I   L   R   V   L   I   W   F   I   S   I   L   A   I ACT GGG AAC ATC ATA GTG CTA GTG ATC CTA ACT ACC AGC CAA
TGA CCC TTG TAG TAT CAC GAT CAC TAG GAT TGA TGG TCG GTT
 T   G   N   I   I   V   L   V   I   L   T   T   S   Q TAT AAA CTC ACA GTC CCC AGG TTC CTT ATG TGC AAC CTG GCC
ATA TTT GAG TGT CAG GGG TCC AAG GAA TAC ACG TTG GAC CGG
 Y   K   L   T   V   P   R   F   L   M   C   N   L   A TTT GCT GAT CTC TGC ATT GGA ATC TAC CTG CTG CTC ATT GCA
AAA CGA CTA GAG ACG TAA CCT TAG ATG GAC GAC GAG TAA CGT
 F   A   D   L   C   I   G   I   Y   L   L   L   I   A TCA GTT GAT ATC CAT ACC AAG AGC CAA TAT CAC AAC TAT GCG
AGT CAA CTA TAG GTA TGG TTC TCG GTT ATA GTG TTG ATA CGC
 S   V   D   I   H   T   K   S   Q   Y   H   N   Y   A AT PvuI C   GAC TGG CAA ACT GGG GCA GGC TGT GAT GCT GCT
TA G    CTG ACC GTT TGA CCC CGT CCG ACA CTA CGA CGA
 I          D   W   Q   T   G   A   G   C   D   A   A GGC TTT TTC ACT GTC TTT GCC AGT GAG CTG TCA GTC TAC ACT
CCG AAA AAG TGA CAG AAA CGG TCA CTC GAC AGT CAG ATG TGA
 G   F   F   T   V   F   A   S   E   L   S   V   Y   T CTG ACA GCT ATC ACC TTG GAA AGA TGG CAT ACC ATC ACG CAT
GAC TGT CGA TAG TGG AAC CTT TCT ACC GTA TGG TAG TGC GTA
 L   T   A   I   T   L   E   R   W   H   T   I   T   H GCC ATG CAG CTG GAC TGC AAG GTG CAG CTC CGC CAT GCT GCC
CGG TAC GTC GAC CTG ACG TTC CAC GTC GAG GCG GTA CGA CGG
 A   M   Q   L   D   C   K   V   Q   L   R   H   A   A AGT GTC ATG GTG ATG GGC TGG ATT TTT GCT TTT GCA GCT GCC
TCA CAG TAC CAC TAC CCG ACC TAA AAA CGA AAA CGT CGA CGG
 S   V   M   V   M   G   W   I   F   A   F   A   A   A CTC TTT CCC ATC TTT GGC ATC AGC AGC TAC ATG AAG GTG AGC
GAG AAA GGG TAG AAA CCG TAG TCG TCG ATG TAC TTC CAC TCG
 L   F   P   I   F   G   I   S   S   Y   M   K   V   S ATC TGC CTG CCC ATG GAT ATT GAC AGC CCT TTG TCA CAG CTG
TAG ACG GAC GGG TAC CTA TAA CTG TCG GGA AAC AGT GTC GAC
 I   C   L   P   M   D   I   D   S   P   L   S   Q   L TAT GTC ATG TCC CTC CTT GTG CTC AAT GTC CTG GCC TTT GTG
ATA CAG TAC AGG GAG GAA CAC GAG TTA CAG GAC CGG AAA CAC
 Y   V   M   S   L   L   V   L   N   V   L   A   F   V
```

```
GTC ATC TGT GGC TGC TAT ATC CAC ATC TAC CTC ACA GTG CGG
CAG TAG ACA CCG ACG ATA TAG GTG TAG ATG GAG TGT CAC GCC
 V   I   C   G   C   Y   I   H   I   Y   L   T   V   R

AAC CCC AAC ATC GTG TCC TCC TCT AGT GAC ACC AGG ATC GCC
TTG GGG TTG TAG CAC AGG AGG AGA TCA CTG TGG TCC TAG CGG
 N   P   N   I   V   S   S   S   D   T   R   I   A

AAG CGC ATG GCC ATG CTC ATC TTC ACT GAC TTC CTC TGC ATG
TTC GCG TAC CGG TAC GAG TAG AAG TGA CTG AAG GAG ACG TAC
 K   R   M   A   M   L   I   F   T   D   F   L   C   M

GCA CCC ATT TCT TTC TTT GCC ATT TCT GCC TCC CTC AAG GTG
CGT GGG TAA AGA AAG AAA CGG TAA AGA CGG AGG GAG TTC CAC
 A   P   I   S   F   F   A   I   S   A   S   L   K   V

CCC CTC ATC ACT GTG TCC AAA GCA AAG ATT CTG CTG GTT CTG
GGG GAG TAG TGA CAC AGG TTT CGT TTC TAA GAC GAC CAA GAC
 P   L   I   T   V   S   K   A   K   I   L   L   V   L

TTT CAC CCC ATC AAC TCC TGT GCC AAC CCC TTC CTC TAT GCC
AAA GTG GGG TAG TTG AGG ACA CGG TTG GGG AAG GAG ATA CGG
 F   H   P   I   N   S   C   A   N   P   F   L   Y   A

ATC TTT ACC AAA AAC TTT CGC AGA GAT TTC TTC ATT CTG CTG
TAG AAA TGG TTT TTG AAA GCG TCT CTA AAG AAG TAA GAC GAC
 I   F   T   K   N   F   R   R   D   F   F   I   L   L

AGC AAG TGT GGC TGC TAT GAA ATG CAA GCC CAA ATT TAT AGG
TCG TTC ACA CCG ACG ATA CTT TAC GTT CGG GTT TAA ATA TCC
 S   K   C   G   C   Y   E   M   Q   A   Q   I   Y   R

ACA GAA ACT TCA TCC ACT GTC CAC AAC ACC CAT CCG C    Sac
TGT CTT TGA AGT AGG TGA CAG GTG TTG TGG GTA GG
 T   E   T   S   S   T   V   H   N   T   H   P

II GG AAT GGC CAC TGC TCT TCA GCT CCC AGA GTC ACC AAT
C GCC TTA CCG GTG ACG AGA AGT CGA GGG TCT CAG TGG TTA
   R   N   G   H   C   S   S   A   P   R   V   T   N

GGT TCC ACT TAC ATA CTT GTC CCT CTA AGT CAT TTA GCC CAA
CCA AGG TGA ATG TAT GAA CAG GGA GAT TCA GTA AAT CGG GTT
 G   S   T   Y   I   L   V   P   L   S   H   L   A   Q

AAC TAA GC NotI
TTG ATT CGCCGG
 N   *
```

Two of the three LIBRARY oligonucleotides are also need to be modified as follows: coding strand LIBRARY-4: SEQ ID NO:39: 5'-PO₄-GTG GTG AGC NNS NNS NNS NNS NNS AAC CCC AAT GAT AAA TAT GAA CCC TT-3'; and complementary strand LIBRARY-S: SEQ ID NO:40: 5'-PO₄-GCT CAC CAC GCC-3'.

The nucleotide sequence of the assembled LIBRARY-4, -5 and -3 oligonucleotides to be ligated into the two PflMI sites of the insert, substituting for the sequence corresponding to FLAG—CONNECT-SENSE/CONNECT-ANTI-SENSE is shown below (sense, SEQ ID NO:39; antisense, SEQ ID NO:40 and SEQ ID NO:30; amino acid, SEQ ID NO:41):

```
Pfl M I GTG GTG AGC NNS NNS NN9 NNS NNS AAC CCC AAT GAT
CCG CAC CAC TCG                                     CTA
   G   V   V   S   X   X   X   X   X   N   P   N   D

AAA TAT GAA CCC TT Pfl M I
TTT ATA CTT GG
 K   Y   E   P   F
```

The DNA sequence is shown in SEQ ID NO:39. This sequence is the same as SEQ ID NO:31 except that it has a "silent" mutation that creates another PflMI restriction site. The DNA sequence (SEQ ID NO:39) is the sequence that would encode the amino acid sequence (SEQ ID NO:41) of the chimeric preprotein that is prolactin signal peptide/FLAG epitope tag/hTHR receptor amino terminus corresponding to amino acid residues 34 to 96 in the native receptor/hFSH receptor sequence from amino acid residue 361 to 694 of the native hFSH receptor. There are three nonsense ("stop") codons (one in each potential reading frame) in the middle of the sequence encoding the hTHR receptor amino terminus that are present to prevent translation of this precursor sequence if this sequence persisted, that is remained uncut, during construction of the final library. These "stop" codons, therefore, would prevent translation of non-recombinant protein. To construct the library, this sequence (SEQ ID NO:39) is cut with PflMI to excise two small DNA fragments flanked by two PflMI restriction sites that is replaced with the following DNA sequences:sense, SEQ ID NO:39; antisense, SEQ ID NO:40 and SEQ ID NO:30) that encodes the pentapeptide library (SEQ ID NO:41).

EXAMPLE II

Peptide Agonists of hCTR

FIG. 6 illustrates the putative two-dimensional topology of a human calcitonin receptor (hCTR). The top of the diagram represents the extracellular (EC) space, the middle portion represents the transmembrane (TM) domain, and the bottom portion represents the intracellular (IC) space. Each circle represents a single amino acid residue designated by the single letter code. The residues specifically referred to in this application are numbered with regard to hCTR-2. Bold lines demarcate the 3 isoforms: hCTR-1—all residues; hCTR-2—missing the 16 amino acids between R174 and S175; and hCTR-3—missing residues 1–47.

To discover small peptides that can serve as agonists for hCTR, a combinatorial peptide library was constructed that expresses random pentapeptides tethered to the seven TM helical bundle of hCTR. A pentapeptide library was chosen based on the fact that TRH is a tripeptide that is blocked at both ends (3+2 (for block)=5) and the resulting number of clones is workable. The constructed library contains all 20 natural amino acids at each of the five positions and therefore has a complexity of $20^5=3.2\times10^6$ possible combinations.

To this end, the complementary DNA (cDNA) sequence that normally encodes hCTR's N-terminal EC domain is substituted by a DNA sequence that encodes the thrombin receptor's N-terminal ectodomain. The chimeric ThrR/hCTR has the variable pentapeptide sequence substituting for the native peptide sequence that is normally unmasked by thrombin action and constitutes the ThrR peptide agonist, but it retains thrombin binding sequences and the thrombin-specific cleavage site. Therefore, the N-terminus of expressed receptors are cleaved by thrombin at the appropriate location exposing a new N-terminus that is made of the variable pentapeptide segment of the library tethered to the remainder of hCTR, that is, in a position that in the native ThrR allows it to serve as an agonist.

To monitor for cell surface expression and for efficient cleavage by thrombin of the N-terminal end of the chimeric receptors, the FLAG epitope is positioned proximally to the thrombin cleavage site. Abs that recognize ThrR N-terminus distal to the position corresponding to the library are also used. Consequently, chimeric receptors expressed on the cell surface are detectable by the appropriate use of both Abs before thrombin treatment, but only with Abs against the distal part after thrombin treatment. This confirms cell-surface expression and adequacy of thrombin generation of potential agonists.

The cDNA sequence encoding the new N-terminus of the chimeric ThrR/hCTR, consisting of a prolactin leader or signal peptide, followed by the FLAG epitope, followed by the N-terminus of the mature human ThrR and the pentapeptide library is constructed by gene synthesis. It consists of a DNA segment of approximately 300 base pairs encoding 100 amino acids that is ligated in frame through an appropriate restriction endonuclease cleavage site that is in the synthetic hCTR-2 cDNA at a position encoding the amino acids that constitute the transition between the N-terminus and the first TM domain. After ligation into a mammalian expression vector, *Escherichia coli* is transformed by electroporation and the transformants are subdivided into pools whose maximal workable complexity is determined according to the efficiency of expression and/or sensitivity of the detection system.

The success of expression cloning strategies, such as the one of the subject invention, is dependent on the reporter (or detection) system used. An amplified reporter system is used in accordance with the subject invention which is based on the second messenger systems triggered by hCTR. hCTR is a GPCR that upon activation in COS-1 cells couples through the G protein, $G_S$, to the enzyme adenylyl cyclase, causing an increase in intracellular concentrations of cyclic AMP (cAMP) and through Gq to the enzyme phospholipase C causing increases in inositol 1,4,5-trisphosphate (IP3), which causes a rise in intracellular free $Ca^2+$, and 1,2-diacylglycerol (DAG) (Nussenzveig et al. 1994). cAMP activates cAMP-dependent protein kinase (PKA), an important intracellular regulator. One PKA substrate is a transcription factor known as cAMP-response element binding protein, CREB, that when activated binds and activates transcription by promoters that contain regulatory sequences known as cAMP-response elements (CREs). A similar cascade initiated by IP3, DAG and an elevation of cytoplasmic $Ca^2+$ that involves other protein kinases triggers gene induction through other motifs using other transcription factors, such as the fos-jun-AP-1 system. This type of reporter system is able to detect basal as well as CT-stimulated activation of the wild type hCTR by using a reporter plasmid containing a minimal promoter of human c-fos gene into which a CREB binding motif (Montminy et al. 1990) was engineered driving transcription of the gene for the enzyme luciferase (pCRE/LUC), whose activity is easily detected by a chemiluminescent reaction. Unfortunately, the use of the enzyme activity of the luciferase reporter system requires the preparation of cell extracts and, therefore, monitors induction in a population of cells. To be able to measure a single positive in a very large number of negatives from a library, a single cell assay is needed. Two different assays are used so as to improve the likelihood of identifying positive clones.

One assay is based on gene induction in COS-1 cells. β-galactosidase is used as a reporter gene in transfected COS-1 cells. This assay takes advantage of the amplification of the enzyme activity of the reporter, with an easily determined color reaction as endpoint, and of the overexpression of receptors with tethered agonists in COS-1 cells because of replication of the plasmids introduced. These experiments were performed by co-transfecting portions of the library and CRE/β-galactosidase or AP-1/β-galactosidase constructs into COS-1 cells so as to amplify expression by plasmid replication using the simian virus-40 origin of replication in the vector. This enhances the signal/noise ratio substantially. Both promoter types are used as hCTR-2 transduces signals by both pathways in COS-1 cells. The signal is further increased because the construct used has a nuclear localization signal ligated to the β-galactosidase that allows the protein to concentrate in the nucleus (Hersh et al. 1995). Single clones that exhibit activation of chimeric ThrR/hCTR after thrombin addition to cleave the N-terminus and expose the tethered agonist, as measured by increased color reaction, are isolated using sib selection, which consists of successive subdivision and amplification of positive pools of clones. The optimal time after thrombin addition to measure the reporter gene activity is determined, as this involves a prolonged response on gene induction and the kinetics of this response vary with different activators (receptors) and in different cells. The optimal time will likely be 4 hrs as that was optimal for sCT stimulation in COS-1 cells co-transfected with hCTR-2 and luciferase under the control of a cAMP-responsive promoter (CRE-LUC). Even though hCTR-2 exhibits constitutive activity, gene expression can be further activated with agonist.

The second reporter system uses Xenopus laevis oocytes. This system, which was used to clone the TRH receptor cDNA (Straub et al. 1990), is dependent on coupling to Gq. In this assay system, individual oocytes are injected with RNA that was transcribed in vitro from pools of plasmids from the library. After one to three days (the optimal time for responsiveness is determined in preliminary experiments with hCTR-2), the responsiveness of the oocytes to thrombin is measured. Thrombin acutely activates receptors in those oocytes expressing chimeric constructs in which the peptide can serve as a tethered agonist. Receptor activation is monitored by acute effects on a chloride current or on stimulation of radiocalcium efflux. Both endpoints are rapid, amplified processes in oocytes. Single clones that exhibit activation of chimeric ThrR/hCTR after thrombin addition are isolated using sib selection. Using both reporter systems allows the determination of whether rapid or more prolonged effects yield better signal-to-noise ratios.

Other reporting systems may also be useful in the cloning strategy, such as an immunofluorescence/ immunocytochemical approach in COS-1 cells that also relies on gene induction. Commercially available anti-GFP Abs (Clontech) or anti-β-galactosidase Abs (Promega Biotech, Inc.) can be used to identify transfected COS-1 cells in which ectopic gene expression has been induced. Or, a plasmid can be constructed in which CRE or AP-1 drives expression of a cell-surface protein to which Abs are available, such as nerve growth factor receptor (Johnson et al. 1986), and FACS sorting can be used to identify positive cells. Alternatively, a rapid effect of activation of the ThrR/ hCTR in COS-1 cells can be monitored. Stimulation of an acute elevation in cytoplasmic $Ca^{2+}$ using Fluo-3 (Molecular Probes) and fluorescence microscopy can be measured. Fluorescent calcium indicators (Geras Raaka and Gershengorn 1987) can be used.

The strategy in accordance with the subject invention for the design of the library suits the purpose for which it is intended to be used because: i) It removes the putative EC N-terminal domain of hCTR to which intact, native CT binds with high affinity. Without hCTR's N-terminus, the possibility of finding a peptide that acts indirectly through hCTR's N-terminus is eliminated. ii) It produces receptors that activate only upon addition of thrombin. This allows for receptors to be active only during the experimental period, avoiding the cellular counterregulatory mechanisms associated with prolonged stimulation (desensitization, down regulation), which can attenuate the detecting signal. iii) A tethered agonist increases the local effective concentration of the ligand enormously. This reduces the possibility that peptide antagonists, if present in the same pool of an untethered peptide library, could interfere with the detection of peptide agonists.

EXAMPLE III

Peptide Negative Antagonists of a GPCR of HHV-8

This example relates to a newly described GPCR that is encoded in the genome of human herpesvirus-8 (HHV-8) (or Kaposi's sarcoma-associated herpesvirus—KSHV) (Cesarman et al. 1996), which is a virus that was first identified in Kaposi's sarcoma (KS) tissues from patients with AIDS and has now been found in KS tissues from human immunodeficiency virus (HIV)-negative patients, in tissues from patients with Castleman's disease and in some B-cell lymphomas (Chang et al. 1994). This receptor is referred to as HHV8 GPCR. The objective of this example is to identify peptides that are high affinity negative antagonists of this constitutively active HHV8 GPCR. A constitutively active receptor is a receptor that exhibits agonist-independent signalling activity (Lefkowitz et al. 1993). Negative antagonists (or inverse agonists) are compounds that are capable of inhibiting the signalling activity of a constitutively active receptor (Schutz and Freissmuth 1992). Neutral antagonists inhibit the action of agonists but do not affect agonist-independent activity. Neutral antagonists would inhibit signalling by HHV8 GPCR when it is activated by natural or synthetic agonists, for example, interleukin-8 (IL-8) that has been shown to activate HHV8 GPCR in Xenopus laevis oocytes, whereas negative antagonists would inhibit "basal" signalling by HHV8 GPCR.

Figure 7:
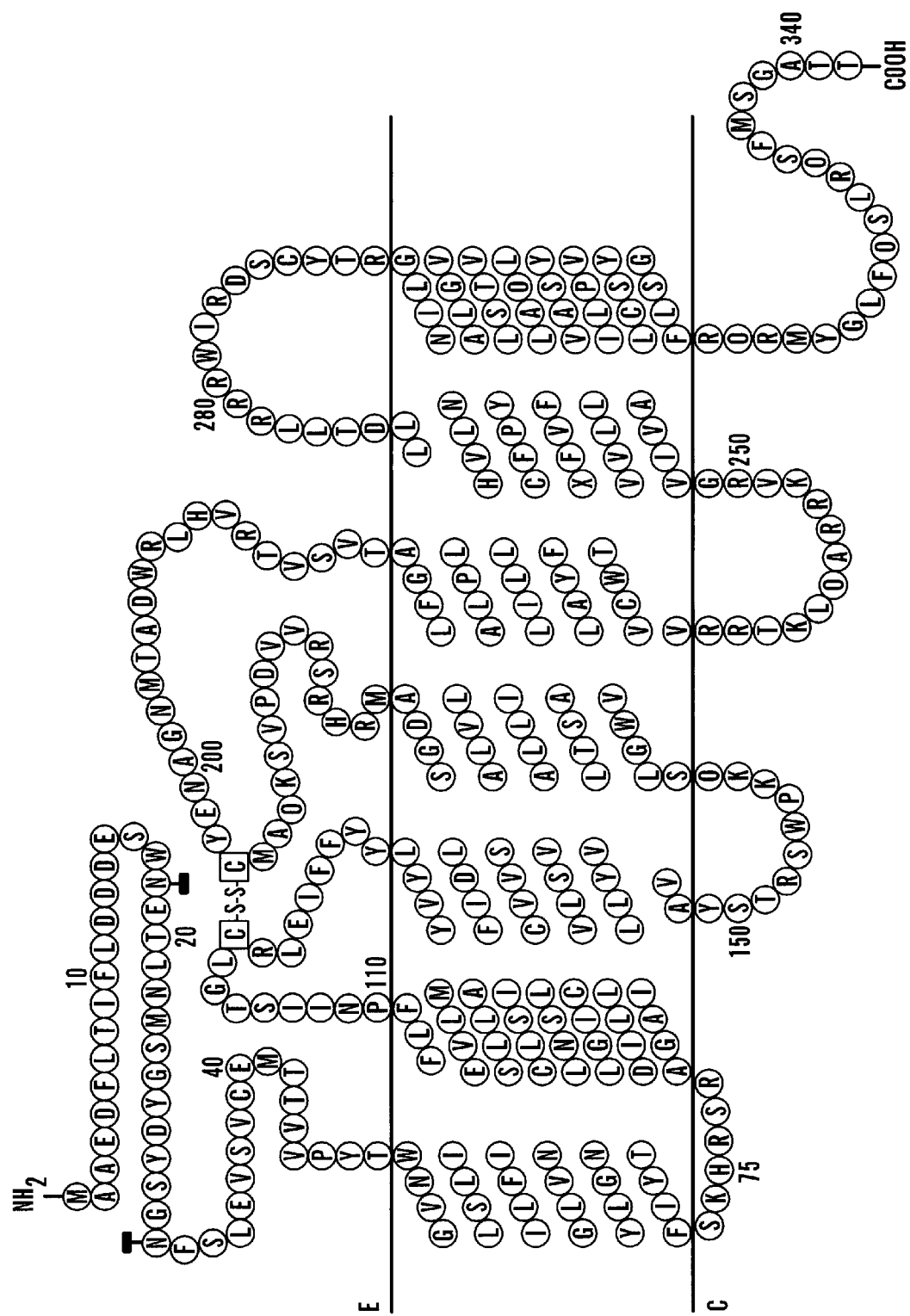
FIG. 7 is a diagram of the putative two-dimensional topology of the human herpesvirus-8 GPCR.
Figure 8:
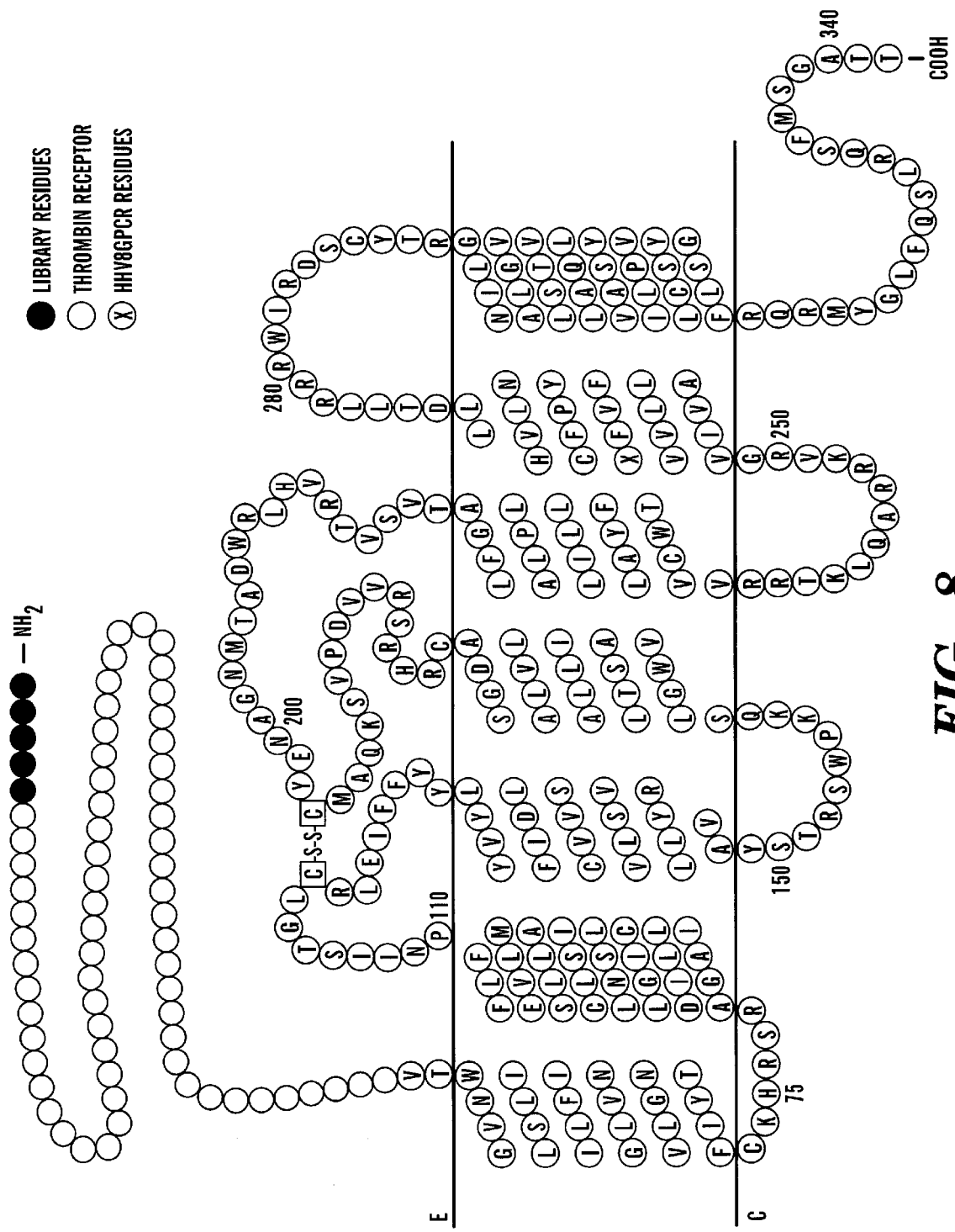
FIG. 8 is a diagram of the putative two-dimensional topology of the chimera ThrR/HHV8 GPCR as it is predicted to be in the cell surface membrane of transfected COS-1 cells.

The HHV8 GPCR is a protein of 342 amino acids that has the features of a GPCR including seven hydrophobic, putative transmembrane-spanning domains (Cesarman et al. 1996). FIG. 7 illustrates the putative two-dimensional topology of HHV8 GPCR in the cell-surface membrane. The top of the diagram represents the extracellular space (E), the middle portion represents the transmembrane (TM) domain and the bottom portion represents the intracellular space (C). Each circle represents an amino acid residue designated by the single letter code. The HHV8 GPCR is a receptor that signals via the phosphoinositide-inositol 1,4,5-trisphosphate-calcium cascade (Berridge 1993).

Discovery of Peptide Negative Antagonists of HHVB GPCR

It is now appreciated that receptors can attain an active conformation in the absence of agonist and manifest constitutive, that is, agonist-independent activity (Lefkowitz et al. 1993). This has led to renewed acceptance of the concept that receptors can change conformation spontaneously and oscillate between active and inactive states (for review, see Leff 1995). Some drugs, termed negative antagonists or inverse agonists, appear capable of constraining receptors in an inactive state (Samama et al. 1994). Negative antagonism is demonstrated when a drug binds to a receptor that exhibits constitutive activity and reduces this activity. It is important to discover agents that exhibit negative antagonistic properties toward HHV8 GPCR to use in exploring the role of HHV8 GPCR during HHV-8 infection in studies in cells in tissue culture and in intact animals.

The subject invention provides a strategy for discovery of small peptide negative antagonists of HHV8 GPCR. A tethered, combinatorial library is used to clone pentapeptides that are negative antagonists of HHV8 GPCR. A pentapeptide library is chosen based on the fact small peptides are effective negative antagonists and the number of clones is workable. The library contains all 20 natural amino acids at each of the five positions and therefore has a complexity of $20^5 3.2 \times 10^6$ possible combinations. This approach is chosen because although there is a good deal of information available regarding IL-8 binding (see above), little is known regarding the specific interactions between IL-8 and IL-8Rs that cause activation (Leong et al. 1994). In fact, this is true for GPCRs in general (Van Rhee and Jacobson 1996). Moreover, there is even less known about specific interactions that may inactivate a constitutively active receptor (Schutz and Freissmuth 1992). Thus, insufficient information is available to "rationally" design small peptides with negative antagonist activities. Thus, discovery of negative antagonist peptides for HHV8 GPCR may best be accomplished by using combinatorial peptide libraries. With this approach, 3.2 million random peptides of five amino acids in length are tested for activity and those that inactivate HHV8 GPCRs are identified by sib selection.

Discovery of High Affinity, Specific Pentapeptide Negative Antagonists of HHV8 GPCR To discover small peptides that can serve as negative antagonists (or inverse agonists) for HHV8 GPCR, a combinatorial peptide library is constructed that expresses random pentapeptides tethered to the seven TM helical bundle of HHV8 GPCR. This strategy is based on the conclusion that one (or several) pentapeptides will interact with the TM bundle or extracellular loops, or both of HHV8 GPCR in a manner similar to that by which other small peptide antagonists interact with other GPCRs, such as receptors for opioid peptides (Costa and Herz 1989; Costa et al. 1992) and bradykinin (Leeb-Lundberg et al. 1994), and by a similar mechanism inactivate HHV8 GPCR.

A pentapeptide library is chosen based on the fact that peptides of this size have been shown to be negative antagonists of other GPCRs and the resulting number of clones is workable. The library contains all 20 natural amino acids at each of the five positions and, therefore, has a complexity of $20^5=3.2\times10^6$ possible compounds. The library is constructed by taking the cDNA sequence of HHV8 GPCR and substituting the sequence that normally encodes HHV8 GPCR's N-terminal extracellular domain by a DNA sequence that encodes the N-terminal ectodomain of the thrombin receptor (ThrR) from just after the activating peptide to the beginning of TM-1; that is, the sequence of the native ThrR from its N-terminus up to and including its activating peptide, Ser-Phe-Leu-Leu-Arg-Asn (SEQ ID NO:43:SFLLRN), is deleted. The chimeric ThrR/HHV8 GPCR primary amino acid sequence begins at its N-terminus with the variable pentapeptide sequence ("library"), which is substituting for SFLLRN, followed by the ThrR amino terminal sequence distal to the SFLLRN sequence (from immediately after SFLLRN to the beginning of TM-1) followed by the HHV8GPCR sequence from the beginning of TM-1 to the carboxyl end (FIG. 8). The distal N-terminal sequence of the ThrR is chosen rather than that of HHV8 GPCR because this sequence allows the pentapeptide library sequences on each ThrR/HHV8 GPCR chimera to be directed into the remainder of the receptor as the exposed N-terminal peptide of ThrR is guided into the receptor's "body". The major difference is that the pentapeptide library is the N-terminus of the ThrR/HHV8 GPCR tethered to the remainder of the receptor, that is, in a position that in the native ThrR allows it to serve as an agonist but allows it in the chimeric receptor to serve as a negative antagonist. No cleavage is necessary to expose the N-terminus pentapeptide sequence. Therefore, the N-terminus of expressed receptors are random pentapeptides that can act as negative antagonists with regard to the constitutive activity of HHV8 GPCRs as soon as the chimeric receptor is expressed. The library is constructed without the need to cleave off a "blocking" sequence in order to expose the pentapeptide because it is desirable for the pentapeptide to inactivate the chimeric receptor as soon as it is expressed on the cell surface. Thus, monitoring is for inactivation of a "basal" signalling activity of the chimeric ThrR/HHV8 GPCR.

FIG. 8 shows the putative topology of the chimera ThrR/HHV8 GPCR as it is predicted to be in the cell surface membrane of transfected COS-1 cells. The top of the diagram represents the extracellular space (E), the middle portion represents the transmembrane (TM) domain and the bottom portion represents the intracellular space (C). The first five filled circles represent individual amino acids that are part of the pentapeptide library; each filled circle represents 20 amino acids. The seventy unfilled circles represent the individual amino acid residues of the native ThrR sequence from just after the activating peptide (SFLLRN) to the beginning of TM-1. Each circle with a letter in it represents an amino acid residue designated by the single letter code of HHV8 GPCR.

To monitor for cell surface expression of the chimeric receptors, antibodies to the extracellular domain of HHV8 GPCR are used, specifically antibodies to the large extracellular loop 2.

The cDNA sequence encoding the new N-terminus of the chimeric ThrR/HHV8 GPCR, consisting of a prolactin leader (or signal) peptide, which is cleaved after directing the protein to the cell surface membrane, followed by the pentapeptide library and the distal sequence of the N-terminus of ThrR is constructed by gene synthesis. It consists of a DNA segment of approximately 210 base pairs encoding 70 amino acids that are ligated in frame through an appropriate restriction endonuclease cleavage site that is created in the HHV8 GPCR cDNA at a position encoding the amino acids that constitute the transition between the N-terminus and the first TM domain. After ligation into a mammalian expression vector, *Escherichia coli* is transformed by electroporation and the transformants are subdivided into pools whose maximal workable complexity is determined according to the efficiency of mammalian cell transfectibn and/or sensitivity of the detection system(s).

The success of expression cloning strategies, such as the one of the subject invention, is dependent on the reporter (or detection) system. An amplified reporter system is used in accordance with the subject invention which is based on the second messenger system triggered by HHV8 GPCR. HHV8 GPCR is a GPCR that in COS-1 cells appears to couple through a G protein to the enzyme phospholipase C causing generation of the second messengers inositol 1,4,5-trisphosphate ($IP_3$), which causes a rise in intracellular free $Ca^{2+}$, and 1,2-diacylglycerol, which activates protein kinase C (Nussenzveig et al. 1994). Activated protein kinase C triggers gene induction through specific motifs using transcription factors, such as the fos-jun-AP-1 system (Deutsch et al. 1990; Schadlow et al. 1992). This reporter system works in COS-1 cells since constitutive activity of HHV8 GPCR is detected using a reporter plasmid containing a minimal promoter of the human c-fos gene into which a AP-1 binding motif is engineered driving transcription of the gene for the enzyme luciferase (pAP-1/LUC), whose activity is detected by a chemiluminescent reaction. Unfortunately, the use of the enzyme activity of the luciferase reporter system requires the preparation of cell extracts and, therefore, monitors induction in a population of cells. To be able to identify receptors that are turned off by negative antagonistic activity of the tethered pentapeptide, a single "hit" in a very large number of negatives needs to be measured. Therefore, a single cell assay is needed. For the reporter, luciferase is replaced with β-galactosidase that can be readily measured in individual cells.

A two-reporter system was devised for discovery of negative antagonists that use gene induction in COS-1 cells. β-galactosidase is used as a reporter enzyme in transfected COS-1 cells. This assay takes advantage of the amplification of the enzyme activity of the reporter, with an easily determined color reaction as endpoint, and of the overexpression of receptors with tethered negative antagonists in COS-1 cells because of replication of the plasmids introduced. These experiments are performed by co-transfecting portions of the plasmid library and a plasmid encoding AP-1/β-galactosidase constructs into COS-1 cells so as to amplify expression by plasmid replication using the simian virus-40 origin of replication in the vector. This enhances the signal/noise ratio substantially. The signal is further increased because the construct used has a nuclear localization signal ligated to the β-galactosidase that allows the protein to concentrate in the nucleus (Hersh et al. 1995). The construct containing β-galactosidase with a nuclear localization signal was shown to express in the nucleus of transfected COS-1 cells. Single clones that exhibit negative antagonistic activity, as measured by decreased color reaction, are isolated using sib selection, which consists of successive subdivision and amplification of positive pools of clones. The optimal time after transfection to assay β-galactosidase activity is determined empirically as this involves a prolonged response on gene induction and the kinetics of this response vary with different activators (receptors) and in different cells.

A second reporter gene is used to identify cells that have been transfected and are expressing foreign proteins to distinguish them from cells that have not been transfected. This is a crucial distinction for this approach because differentiation between cells that have the capacity to express the specific reporter gene but are not (or in which expression has been diminished) because transcription has been inhibited, from cells that are not expressing the reporter gene because they are not transfected, is necessary. Because the β-galactosidase activity is expressed in the nucleus, it has a different localization than the nonspecific reporter of transfection. The nonspecific reporter of transfection is a construct containing a mutant of the human placental alkaline phosphatase gene (Tate et al. 1990) that is targeted to the cytoplasm under the control of a cytomegalovirus promoter; this promoter is not affected by HHV8 GPCR and is active in all transfected cells. Thus, one can monitor for 3 types of cells: 1) cells in which β-galactosidase is expressed at high levels in the nucleus and alkaline phosphatase is expressed in the cytoplasm—these are transfected cells that do not express receptors that contain a peptide that has negative antagonistic activity because expression of β-galactosidase is induced by the constitutive signalling activity of HHV8 GPCR; 2) cells in which β-galactosidase is not expressed in the nucleus and alkaline phosphatase is not expressed in the cytoplasm—these are cells that have not been transfected; and 3) cells in which β-galactosidase is not expressed (or is expressed at low levels in the nucleus) and alkaline phosphatase is expressed in the cytoplasm—these are transfected cells that express receptors that contain a peptide that has negative antagonistic activity.

Other reporting systems may also be useful in the cloning strategy, such as the yeast bioassay system discussed above or an immunofluorescence/immunocytochemical approach in COS-1 cells that also relies on gene induction. Commercially available anti-β-galactosidase antibodies (Promega Biotech, Inc.) can be used to identify transfected COS-1 cells in which ectopic gene expression has been modulated. Or, a plasmid can be constructed in which AP-1 drives the expression of a cell-surface protein to which Abs are available, such as the nerve growth factor receptor (Johnson et al. 1986).

The strategy devised in the design of the library suits the purpose for which it is intended to be used, because a tethered negative antagonist increases the local effective concentration of the ligand enormously. This also reduces the possibility that neutral antagonists or agonists, if present in the same pool of an untethered peptide library, could interfere with the detection of peptide negative antagonists.

Although preferred embodiments have been depicted and described in detail herein, it will be apparent to those of ordinary skill in the relevant art that various modifications, additions, substitutions and the like can be made without departing from the spirit of the invention and these are therefore considered to be within the scope of the invention as defined in the claims which follow.

LIST OF REFERENCES CITED

Berridge, M. J., Nature 365:388–389 (1993).
Bordo, D., and Argos, P., J Mol Biol 217:721–729 (1991).
Cascieri, M. A., et al., J Pharmacol Toxicol Methods 33:179–185 (1995).
Cesarman, E., et al., J Virol 70:8218–8223 (1996).
Chang, Y., et al., Science 266:1865–1869 (1994).
Chen, J., et al., J Biol Chem 270:23398–23401 (1995).
Costa, T. and Herz, A., Proc Natl Acad Sci USA 86:7321–7325 (1989).
Costa, T., et al., Mol Pharmacol 41:549–560 (1992).
Deutsch, P. J., et al., J Biol Chem 265:10274–10281
Dohlman, H. G., et al., Annu Rev Biochem 60:653–688 (1991).
French, S., and Robson, B., J Molecular Evolution 19:171–175 (1983).
Geras Raaka, E., and Gershengorn, M. C., Methods Enzymol 141:36–53 (1987).
Gershengorn, M. C., and Osman, R., Physiol Rev 76:175–191 (1996).
Heinflink, M., et al., Molecular Endocrinology 9:1455–1460 (1995).
Hersh, J., et al., Gene Therapy 2:124–131 (1995).
Johnson, D., et al., Cell 47:545–554 (1986).
King, K., et al., Science 250:121–123 (1990).
Leeb-Lundberg, L. M. F., et al., J Biol Chem 269:25970–25973 (1994).
Leff, P., Trends Pharmacol Sci 16:89–97 (1995).
Lefkowitz, R. J., et al., Trends Pharmacol Sci 14:303–307 (1993).
Leong, S. R., et al., J Biol Chem 269:19343–19348 (1994).
Liu, G., et al., Biochemistry 35:197–201 (1996).
Montminy, M. R., et al., TINS 13:184–188 (1990).
Nussenzveig, D. R., et al., J Biol Chem 269:28123–28129 (1994).
Perez, H. D., et al., J Biol Chem 269:22485–22487 (1994).
Price, L. A., et al., Mol Cell Biol 15:6188–6195 (1995).
Price, L. A., et al., Mol Pharmacol 50:829–837 (1996).
Samama, P., et al., Mol Pharmacol 45:390–394 (1994).
Sambrook et al., *Molecular Cloning: A Laboratory Manual*, 2d Edition, Cold Spring Harbor Laboratory Press, Cold Spring Harbor, New York (1989).
Schadlow, V., et al., Mol Biol Cell 3:941–951 (1992).
Schutz, W., and Freissmuth, M., Trends Pharmacol Sci 13:376–380 (1992).
Straub, R. E., et al., Proc Natl Acad Sci USA 87:9514–9518 (1990).

Stroop, S. D., et al., Biochemistry 34:1050–1057 (1995).

Tapparelli, C., et al., Trends Pharmacol Sci 14:426–428 (1993).

Tate, S. S., et al., FASEB J 4:227–231 (1990).

Taylor, W. R., J Theor Biol 119:205–218 (1986).

Van Rhee, A. M., and Jacobson, K. A., Drug Dev Res 37:1–38 (1996).

---

SEQUENCE LISTING (1) GENERAL INFORMATION:

(iii) NUMBER OF SEQUENCES: 44

(2) INFORMATION FOR SEQ ID NO:1:

(i) SEQUENCE CHARACTERISTICS:
      (A) LENGTH: 63 amino acids
      (B) TYPE: amino acid
      (C) STRANDEDNESS: Not Relevant
      (D) TOPOLOGY: linear (ii) MOLECULE TYPE: peptide (xi) SEQUENCE DESCRIPTION: SEQ ID NO:1:

```
Leu Asp Ala Thr Leu Asp Pro Arg Ser Phe Leu Leu Arg Asn Pro Asn
1               5                  10                  15

Asp Lys Tyr Glu Pro Phe Trp Glu Asp Glu Glu Lys Asn Glu Ser Gly
            20                  25                  30

Leu Thr Glu Tyr Arg Leu Val Ser Ile Asn Lys Ser Ser Pro Leu Gln
        35                  40                  45

Lys Gln Leu Pro Ala Phe Ile Ser Glu Asp Ala Ser Gly Tyr Leu
    50                  55                  60
```

(2) INFORMATION FOR SEQ ID NO:2:

(i) SEQUENCE CHARACTERISTICS:
      (A) LENGTH: 436 amino acids
      (B) TYPE: amino acid
      (C) STRANDEDNESS: Not Relevant
      (D) TOPOLOGY: linear (ii) MOLECULE TYPE: peptide (xi) SEQUENCE DESCRIPTION: SEQ ID NO:2:

```
Met Asp Ser Lys Gly Ser Ser Gln Lys Gly Ser Arg Leu Leu Leu Leu
1               5                  10                  15

Leu Val Val Ser Asn Leu Leu Leu Cys Gln Gly Val Val Ser Asp Tyr
            20                  25                  30

Lys Asp Asp Asp Lys Leu Asp Ala Thr Leu Asp Pro Arg Xaa Xaa
        35                  40                  45

Xaa Xaa Xaa Asn Pro Asn Asp Lys Tyr Glu Pro Phe Trp Glu Asp Glu
    50                  55                  60

Glu Lys Asn Glu Ser Gly Leu Thr Glu Tyr Arg Leu Val Ser Ile Asn
65                  70                  75                  80

Lys Ser Ser Pro Leu Gln Lys Gln Leu Pro Ala Phe Ile Ser Glu Asp
            85                  90                  95

Ala Ser Gly Tyr Leu Gly Tyr Asn Ile Leu Arg Val Leu Ile Trp Phe
            100                 105                 110

Ile Ser Ile Leu Ala Ile Thr Gly Asn Ile Ile Val Leu Val Ile Leu
        115                 120                 125

Thr Thr Ser Gln Tyr Lys Leu Thr Val Pro Arg Phe Leu Met Cys Asn
    130                 135                 140
```

```
Leu Ala Phe Ala Asp Leu Cys Ile Gly Ile Tyr Leu Leu Leu Ile Ala
145                 150                 155                 160

Ser Val Asp Ile His Thr Lys Ser Gln Tyr His Asn Tyr Ala Ile Asp
                165                 170                 175

Trp Gln Thr Gly Ala Gly Cys Asp Ala Ala Gly Phe Phe Thr Val Phe
            180                 185                 190

Ala Ser Glu Leu Ser Val Tyr Thr Leu Thr Ala Ile Thr Leu Glu Arg
        195                 200                 205

Trp His Thr Ile Thr His Ala Met Gln Leu Asp Cys Lys Val Gln Leu
    210                 215                 220

Arg His Ala Ala Ser Val Met Val Met Gly Trp Ile Phe Ala Phe Ala
225                 230                 235                 240

Ala Ala Leu Phe Pro Ile Phe Gly Ile Ser Ser Tyr Met Lys Val Ser
                245                 250                 255

Ile Cys Leu Pro Met Asp Ile Asp Ser Pro Leu Ser Gln Leu Tyr Val
                260                 265                 270

Met Ser Leu Leu Val Leu Asn Val Leu Ala Phe Val Val Ile Cys Gly
            275                 280                 285

Cys Tyr Ile His Ile Tyr Leu Thr Val Arg Asn Pro Asn Ile Val Ser
        290                 295                 300

Ser Ser Ser Asp Thr Arg Ile Ala Lys Arg Met Ala Met Leu Ile Phe
305                 310                 315                 320

Thr Asp Phe Leu Cys Met Ala Pro Ile Ser Phe Phe Ala Ile Ser Ala
                325                 330                 335

Ser Leu Lys Val Pro Leu Ile Thr Val Ser Lys Ala Lys Ile Leu Leu
            340                 345                 350

Val Leu Phe His Pro Ile Asn Ser Cys Ala Asn Pro Phe Leu Tyr Ala
        355                 360                 365

Ile Phe Thr Lys Asn Phe Arg Arg Asp Phe Phe Ile Leu Leu Ser Lys
    370                 375                 380

Cys Gly Cys Tyr Glu Met Gln Ala Gln Ile Tyr Arg Thr Glu Thr Ser
385                 390                 395                 400

Ser Thr Val His Asn Thr His Pro Arg Asn Gly His Cys Ser Ser Ala
                405                 410                 415

Pro Arg Val Thr Asn Gly Ser Thr Tyr Ile Leu Val Pro Leu Ser His
            420                 425                 430

Leu Ala Gln Asn
        435

(2) INFORMATION FOR SEQ ID NO:3:

(i) SEQUENCE CHARACTERISTICS:
        (A) LENGTH: 30 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:3:

Met Asp Ser Lys Gly Ser Ser Gln Lys Gly Ser Arg Leu Leu Leu Leu
1               5                   10                  15

Leu Val Val Ser Asn Leu Leu Leu Cys Gln Gly Val Val Ser
            20                  25                  30

(2) INFORMATION FOR SEQ ID NO:4:
```

(i) SEQUENCE CHARACTERISTICS:
            (A) LENGTH: 8 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:4:

Asp Tyr Lys Asp Asp Asp Asp Lys
1               5

(2) INFORMATION FOR SEQ ID NO:5:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:5:

Xaa Xaa Xaa Xaa Xaa
1               5

(2) INFORMATION FOR SEQ ID NO:6:

(i) SEQUENCE CHARACTERISTICS:
            (A) LENGTH: 50 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:6:

AATTCCACCA TGGACTCCAA GGGCTCGAGC CAGAAGGGAT CTAGACTGCT          50

(2) INFORMATION FOR SEQ ID NO:7:

(i) SEQUENCE CHARACTERISTICS:
            (A) LENGTH: 50 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:7:

CAGCAGCAGT CTAGATCCCT TCTGGCTCGA GCCCTTGGAG TCCATGGTGG          50

(2) INFORMATION FOR SEQ ID NO:8:

(i) SEQUENCE CHARACTERISTICS:
            (A) LENGTH: 46 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:8:

GCTGCTGCTG GTGGTGAGCA ACCTGCTGCT GTGCCAGGGC GTCGTG              46

(2) INFORMATION FOR SEQ ID NO:9:

(i) SEQUENCE CHARACTERISTICS:
            (A) LENGTH: 46 base pairs (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:9:

CGCTCACGAC GCCCTGGCAC AGCAGCAGGT TGCTCACCAC CAGCAG        46

(2) INFORMATION FOR SEQ ID NO:10:

(i) SEQUENCE CHARACTERISTICS:
        (A) LENGTH: 40 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:10:

AGCGACTACA AGGACGACGA CGACAAGCTT CCTGCCTTTT        40

(2) INFORMATION FOR SEQ ID NO:11:

(i) SEQUENCE CHARACTERISTICS:
        (A) LENGTH: 38 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:11:

CGAAAAGGCA GGAAGCTTGT CGTCGTCGTC CTTGTAGT        38

(2) INFORMATION FOR SEQ ID NO:12:

(i) SEQUENCE CHARACTERISTICS:
        (A) LENGTH: 54 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:12:

TATGCCACCT TTTGGGAGGA TGAGGAGAAA AATGAAAGTG GGTTAACTGA A TAC        54

(2) INFORMATION FOR SEQ ID NO:13:

(i) SEQUENCE CHARACTERISTICS:
        (A) LENGTH: 56 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:13:

TGAAGAGGAC TGCTTTTATT GATGGAGACT AATCTGTATT CAGTTAACCC A CTTTC        56

(2) INFORMATION FOR SEQ ID NO:14:

(i) SEQUENCE CHARACTERISTICS:
        (A) LENGTH: 55 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:14:

CAATAAAAGC AGTCCTCTTC AAAAACAACT TCCTGCATTC ATCTCAGAAG A TGCC    55

(2) INFORMATION FOR SEQ ID NO:15:

(i) SEQUENCE CHARACTERISTICS:
        (A) LENGTH: 38 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:15:

GTCAGGTAAC CGGAGGCATC TTCTGAGATG AATGCAAG    38

(2) INFORMATION FOR SEQ ID NO:16:

(i) SEQUENCE CHARACTERISTICS:
        (A) LENGTH: 35 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:16:

TGAAGGTTAC CTGGGGTACA ACATCCTCAG AGTCC    35

(2) INFORMATION FOR SEQ ID NO:17:

(i) SEQUENCE CHARACTERISTICS:
        (A) LENGTH: 39 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:17:

TCACGCGGCC GCTTAGTTTT GGGCTAAATG ACTTAGAGG    39

(2) INFORMATION FOR SEQ ID NO:18:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:18:

AATTCGGCTT    10

(2) INFORMATION FOR SEQ ID NO:19:

(i) SEQUENCE CHARACTERISTICS:
        (A) LENGTH: 5 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:19:

AGCCG                                                                5

(2) INFORMATION FOR SEQ ID NO:20:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:20:

CAGTCGATCG CATAGTTGTG ATATTGGCTC                                     30

(2) INFORMATION FOR SEQ ID NO:21:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:21:

AACAGCTATG ACCATG                                                    16

(2) INFORMATION FOR SEQ ID NO:22:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:22:

CCATCCGCGG AATGGCCACT GCTCTTCAGC                                     30

(2) INFORMATION FOR SEQ ID NO:23:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:23:

GTAAAACGAC GGCCAGT                                                   17

(2) INFORMATION FOR SEQ ID NO:24:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:24:

TATGCGATCG ACTGGCAAAC TGGGGCAGG                                      29

(2) INFORMATION FOR SEQ ID NO:25:

(i) SEQUENCE CHARACTERISTICS:
            (A) LENGTH: 29 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:25:

CATTCCGCGG ATGGGTGTTG TGGACAGTG                                                29

(2) INFORMATION FOR SEQ ID NO:26:

(i) SEQUENCE CHARACTERISTICS:
            (A) LENGTH: 45 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:26:

AGCTTGATGC CACGCTATGG CCCTAGGTAA GTGATATGCC ACCTT                              45

(2) INFORMATION FOR SEQ ID NO:27:

(i) SEQUENCE CHARACTERISTICS:
            (A) LENGTH: 38 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:27:

GTGGCATATC ACTTACCTAG GGCCATAGCG TGGCATCA                                      38

(2) INFORMATION FOR SEQ ID NO:28:

(i) SEQUENCE CHARACTERISTICS:
            (A) LENGTH: 36 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:28:

AGATCCCCGG AACCCCAATG ATAAATATGA ACCCTT                                        36

(2) INFORMATION FOR SEQ ID NO:29:

(i) SEQUENCE CHARACTERISTICS:
            (A) LENGTH: 13 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:29:

CCGGGGATCT AGC                                                                 13

(2) INFORMATION FOR SEQ ID NO:30:

(i) SEQUENCE CHARACTERISTICS:
            (A) LENGTH: 14 base pairs
            (B) TYPE: nucleic acid (C) STRANDEDNESS: double
        (D) TOPOLOGY: linear (ii) MOLECULE TYPE: cDNA (xi) SEQUENCE DESCRIPTION: SEQ ID NO:30:

GGTTCATATT TATC                                                        14

(2) INFORMATION FOR SEQ ID NO:31:

(i) SEQUENCE CHARACTERISTICS:
        (A) LENGTH: 1300 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:31:

AATTCCACCA TGGACTCCAA GGGCTCGAGC CAGAAGGGAT CTAGACTGCT G CTGCTGCTG      60

GTGGTGAGCA ACCTGCTGCT GTGCCAGGGC GTCGTGAGCG ACTACAAGGA C GACGACGAC    120

AAGCTTGATG CCACGCTATG GCCCTAGGTA AGTGATATGC CACCTTTTGG G AGGATGAGG    180

AGAAAAATGA AAGTGGGTTA ACTGAATACA GATTAGTCTC CATCAATAAA A GCAGTCCTC    240

TTCAAAAACA ACTTCCTGCA TTCATCTCAG AAGATGCCTC CGGTTACCTG G GGTACAACA    300

TCCTCAGAGT CCTGATATGG TTTATCAGCA TCCTGGCCAT CACTGGGAAC A TCATAGTGC    360

TAGTGATCCT AACTACCAGC CAATATAAAC TCACAGTCCC CAGGTTCCTT A TGTGCAACC    420

TGGCCTTTGC TGATCTCTGC ATTGGAATCT ACCTGCTGCT CATTGCATCA G TTGATATCC    480

ATACCAAGAG CCAATATCAC AACTATGCGA TCGACTGGCA AACTGGGGCA G GCTGTGATG    540

CTGCTGGCTT TTTCACTGTC TTTGCCAGTG AGCTGTCAGT CTACACTCTG A CAGCTATCA    600

CCTTGGAAAG ATGGCATACC ATCACGCATG CCATGCAGCT GGACTGCAAG G TGCAGCTCC    660

GCCATGCTGC CAGTGTCATG GTGATGGGCT GGATTTTTGC TTTTGCAGCT G CCCTCTTTC    720

CCATCTTTGG CATCAGCAGC TACATGAAGG TGAGCATCTG CCTGCCCATG G ATATTGACA    780

GCCCTTTGTC ACAGCTGTAT GTCATGTCCC TCCTTGTGCT CAATGTCCTG G CCTTTGTGG    840

TCATCTGTGG CTGCTATATC CACATCTACC TCACAGTGCG GAACCCCAAC A TCGTGTCCT    900

CCTCTAGTGA CACCAGGATC GCCAAGCGCA TGGCCATGCT CATCTTCACT G ACTTCCTCT    960

GCATGGCACC CATTTCTTTC TTTGCCATTT CTGCCTCCCT CAAGGTGCCC C TCATCACTG   1020

TGTCCAAAGC AAAGATTCTG CTGGTTCTGT TCACCCCAT CAACTCCTGT G CCAACCCCT    1080

TCCTCTATGC CATCTTTACC AAAAACTTTC GCAGAGATTT CTTCATTCTG C TGAGCAAGT   1140

GTGGCTGCTA TGAAATGCAA GCCCAAATTT ATAGGACAGA AACTTCATCC A CTGTCCACA   1200

ACACCCATCC GCGGAATGGC CACTGCTCTT CAGCTCCCAG AGTCACCAAT G GTTCCACTT   1260

ACATACTTGT CCCTCTAAGT CATTTAGCCC AAAACTAAGC                         1300

(2) INFORMATION FOR SEQ ID NO:32:

(i) SEQUENCE CHARACTERISTICS:
        (A) LENGTH: 1298 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:32:

-continued

```
GGCCGCTTAG TTTTGGGCTA AATGACTTAG AGGGACAAGT ATGTAAGTGG A ACCATTGGT       60

GACTCTGGGA GCTGAAGAGC AGTGGCCATT CCGCGGATGG GTGTTGTGGA C AGTGGATGA      120

AGTTTCTGTC CTATAAATTT GGGCTTGCAT TTCATAGCAG CCACACTTGC T CAGCAGAAT      180

GAAGAAATCT CTGCGAAAGT TTTTGGTAAA GATGGCATAG AGGAAGGGGT T GGCACAGGA      240

GTTGATGGGG TGAAACAGAA CCAGCAGAAT CTTTGCTTTG GACACAGTGA T GAGGGCAC       300

CTTGAGGGAG GCAGAAATGG CAAAGAAAGA AATGGGTGCC ATGCAGAGGA A GTCAGTGAA      360

GATGAGCATG GCCATGCGCT TGGCGATCCT GGTGTCACTA GAGGAGGACA C GATGTTGGG      420

GTTCCGCACT GTGAGGTAGA GTGGATATA GCAGCCACAG ATGACCACAA A GGCCAGGAC       480

ATTGAGCACA AGGAGGGACA TGACATACAG CTGTGACAAA GGGCTGTCAA T ATCCATGGG      540

CAGGCAGATG CTCACCTTCA TGTAGCTGCT GATGCCAAAG ATGGGAAAGA G GGCAGCTGC      600

AAAAGCAAAA ATCCAGCCCA TCACCATGAC ACTGGCAGCA TGGCGGAGCT G CACCTTGCA      660

GTCCAGCTGC ATGGCATGCG TGATGGTATG CCATCTTTCC AAGGTGATAG C TGTCAGAGT      720

GTAGACTGAC AGCTCACTGG CAAAGACAGT GAAAAAGCCA GCAGCATCAC A GCCTGCCCC      780

AGTTTGCCAG TCGATCGCAT AGTTGTGATA TTGGCTCTTG GTATGGATAT C AACTGATGC      840

AATGAGCAGC AGGTAGATTC CAATGCAGAG ATCAGCAAAG GCCAGGTTGC A CATAAGGAA      900

CCTGGGGACT GTGAGTTTAT ATTGGCTGGT AGTTAGGATC ACTAGCACTA T GATGTTCCC      960

AGTGATGGCC AGGATGCTGA TAAACCATAT CAGGACTCTG AGGATGTTGT A CCCCAGGTA     1020

ACCGGAGGCA TCTTCTGAGA TGAATGCAGG AAGTTGTTTT TGAAGAGGAC T GCTTTTATT     1080

GATGGAGACT AAACTGTATT CAGTTAACCC ACTTTCATTT TTCTCCTCAT C CTCCCAAAA     1140

GGGCATATCA CTTACCTAGG GCCATAGCGT GGCATCAAGC TTGTCGTCGT C GTCCTTGTA     1200

GTCGCTCACG ACGCCCTGGC ACAGCAGCAG GTTGCTCACC ACCAGCAGCA G CAGCAGTCT     1260

AGATCCCTTC TGGCTCGAGC CCTTGGAGTC CATGGTGG                              1298
```

(2) INFORMATION FOR SEQ ID NO:33:

(i) SEQUENCE CHARACTERISTICS:
        (A) LENGTH: 420 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:33:

```
Met Asp Ser Lys Gly Ser Ser Gln Lys Gly S er Arg Leu Leu Leu
1               5                   10                  15

Leu Val Val Ser Asn Leu Leu Cys Gln G ly Val Val Ser Asp Tyr
                20                  25                  30

Lys Asp Asp Asp Lys Leu Asp Ala Thr L eu Phe Trp Glu Asp Glu
                35                  40                  45

Glu Lys Asn Glu Ser Gly Leu Thr Glu Tyr A rg Leu Val Ser Ile Asn
            50                  55                  60

Lys Ser Ser Pro Leu Gln Lys Gln Leu Pro A la Phe Ile Ser Glu Asp
65                  70                  75                  80

Ala Ser Gly Tyr Leu Gly Tyr Asn Ile Leu A rg Val Leu Ile Trp Phe
                85                  90                  95

Ile Ser Ile Leu Ala Ile Thr Gly Asn Ile I le Val Leu Val Ile Leu
                100                 105                 110

Thr Thr Ser Gln Tyr Lys Leu Thr Val Pro A rg Phe Leu Met Cys Asn
```

-continued

```
            115                 120                  125
Leu Ala Phe Ala Asp Leu Cys Ile Gly Ile T yr Leu Leu Leu Ile Ala
    130                 135                 140

Ser Val Asp Ile His Thr Lys Ser Gln Tyr H is Asn Tyr Ala Ile Asp
145                 150                  155                 160

Trp Gln Thr Gly Ala Gly Cys Asp Ala Ala G ly Phe Phe Thr Val Phe
                165                 170                  175

Ala Ser Glu Leu Ser Val Tyr Thr Leu Thr A la Ile Thr Leu Glu Arg
            180                 185                  190

Trp His Thr Ile Thr His Ala Met Gln Leu A sp Cys Lys Val Gln Leu
            195                 200                  205

Arg His Ala Ala Ser Val Met Val Met Gly T rp Ile Phe Ala Phe Ala
    210                 215                 220

Ala Ala Leu Phe Pro Ile Phe Gly Ile Ser S er Tyr Met Lys Val Ser
225                 230                  235                 240

Ile Cys Leu Pro Met Asp Ile Asp Ser Pro L eu Ser Gln Leu Tyr Val
                245                 250                  255

Met Ser Leu Leu Val Leu Asn Val Leu Ala P he Val Val Ile Cys Gly
            260                 265                  270

Cys Tyr Ile His Ile Tyr Leu Thr Val Arg A sn Pro Asn Ile Val Ser
            275                 280                  285

Ser Ser Ser Asp Thr Arg Ile Ala Lys Arg M et Ala Met Leu Ile Phe
    290                 295                 300

Thr Asp Phe Leu Cys Met Ala Pro Ile Ser P he Phe Ala Ile Ser Ala
305                 310                  315                 320

Ser Leu Lys Val Pro Leu Ile Thr Val Ser L ys Ala Lys Ile Leu Leu
                325                 330                  335

Val Leu Phe His Pro Ile Asn Ser Cys Ala A sn Pro Phe Leu Tyr Ala
            340                 345                  350

Ile Phe Thr Lys Asn Phe Arg Arg Asp Phe P he Ile Leu Leu Ser Lys
            355                 360                  365

Cys Gly Cys Tyr Glu Met Gln Ala Gln Ile T yr Arg Thr Glu Thr Ser
    370                 375                 380

Ser Thr Val His Asn Thr His Pro Arg Asn G ly His Cys Ser Ser Ala
385                 390                  395                 400

Pro Arg Val Thr Asn Gly Ser Thr Tyr Ile L eu Val Pro Leu Ser His
                405                 410                  415

Leu Ala Gln Asn
            420
```

(2) INFORMATION FOR SEQ ID NO:34:

(i) SEQUENCE CHARACTERISTICS:
        (A) LENGTH: 85 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:34:

```
Met Asp Ser Lys Gly Ser Ser Gln Lys Gly S er Arg Leu Leu Leu Leu
1               5                   10                  15

Leu Val Val Ser Asn Leu Leu Leu Cys Gln G ly Val Val Ser Xaa Xaa
            20                  25                  30

Xaa Xaa Xaa Asn Pro Asn Asp Lys Tyr Glu P ro Phe Trp Glu Asp Glu
```

```
            35                  40                  45
Glu Lys Asn Glu Ser Gly Leu Thr Glu Tyr A rg Leu Val Ser Ile Asn
     50                  55                  60

Lys Ser Ser Pro Leu Gln Lys Gln Leu Pro A la Phe Ile Ser Glu Asp
 65                  70                  75                  80

Ala Ser Gly Tyr Leu
             85
```

(2) INFORMATION FOR SEQ ID NO:35:

(i) SEQUENCE CHARACTERISTICS:
        (A) LENGTH: 45 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:35:

```
ATCAAGCTTG TCGTCGTCGT CCTTGTAGTC GCTCACCACG CCCTG            45
```

(2) INFORMATION FOR SEQ ID NO:36:

(i) SEQUENCE CHARACTERISTICS:
        (A) LENGTH: 1300 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:36:

```
AATTCCACCA TGGACTCCAA GGGCTCGAGC CAGAAGGGAT CTAGACTGCT G CTGCTGCTG      60
GTGGTGAGCA ACCTGCTGCT GTGCCAGGGC GTGGTGAGCG ACTACAAGGA C GACGACGAC     120
AAGCTTGATG CCACGCTATG GCCCTAGGTA AGTGATATGC CACCTTTTGG G AGGATGAGG     180
AGAAAAATGA AAGTGGGTTA ACTGAATACA GATTAGTCTC CATCAATAAA A GCAGTCCTC     240
TTCAAAAACA ACTTCCTGCA TTCATCTCAG AAGATGCCTC CGGTTACCTG G GGTACAACA     300
TCCTCAGAGT CCTGATATGG TTTATCAGCA TCCTGGCCAT CACTGGGAAC A TCATAGTGC     360
TAGTGATCCT AACTACCAGC CAATATAAAC TCACAGTCCC CAGGTTCCTT A TGTGCAACC     420
TGGCCTTTGC TGATCTCTGC ATTGGAATCT ACCTGCTGCT CATTGCATCA G TTGATATCC     480
ATACCAAGAG CCAATATCAC AACTATGCGA TCGACTGGCA AACTGGGGCA G GCTGTGATG     540
CTGCTGGCTT TTTCACTGTC TTTGCCAGTG AGCTGTCAGT CTACACTCTG A CAGCTATCA     600
CCTTGGAAAG ATGGCATACC ATCACGCATG CCATGCAGCT GGACTGCAAG G TGCAGCTCC     660
GCCATGCTGC CAGTGTCATG GTGATGGGCT GGATTTTTGC TTTTGCAGCT G CCCTCTTTC     720
CCATCTTTGG CATCAGCAGC TACATGAAGG TGAGCATCTG CCTGCCCATG G ATATTGACA     780
GCCCTTTGTC ACAGCTGTAT GTCATGTCCC TCCTTGTGCT CAATGTCCTG G CCTTTGTGG     840
TCATCTGTGG CTGCTATATC CACATCTACC TCACAGTGCG GAACCCCAAC A TCGTGTCCT     900
CCTCTAGTGA CACCAGGATC GCCAAGCGCA TGGCCATGCT CATCTTCACT G ACTTCCTCT     960
GCATGGCACC CATTTCTTTC TTTGCCATTT CTGCCTCCCT CAAGGTGCCC C TCATCACTG    1020
TGTCCAAAGC AAAGATTCTG CTGGTTCTGT TCACCCCCAT CAACTCCTGT G CCAACCCCT    1080
TCCTCTATGC CATCTTTACC AAAAACTTTC GCAGAGATTT CTTCATTCTG C TGAGCAAGT    1140
GTGGCTGCTA TGAAATGCAA GCCCAAATTT ATAGGACAGA AACTTCATCC A CTGTCCACA    1200
```

| ACACCCATCC GCGGAATGGC CACTGCTCTT CAGCTCCCAG AGTCACCAAT G GTTCCACTT | 1260 |
| ACATACTTGT CCCTCTAAGT CATTTAGCCC AAAACTAAGC | 1300 |

(2) INFORMATION FOR SEQ ID NO:37:

(i) SEQUENCE CHARACTERISTICS:
        (A) LENGTH: 1300 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:37:

| GGCCGCTTAG TTTTGGGCTA AATGACTTAG AGGGACAAGT ATGTAAGTGG A ACCATTGGT | 60 |
| GACTCTGGGA GCTGAAGAGC AGTGGCCATT CCGCGGATGG GTGTTGTGGA C AGTGGATGA | 120 |
| AGTTTCTGTC CTATAAATTT GGGCTTGCAT TTCATAGCAG CCACACTTGC T CAGCAGAAT | 180 |
| GAAGAAATCT CTGCGAAAGT TTTTGGTAAA GATGGCATAG AGGAAGGGGT T GGCACAGGA | 240 |
| GTTGATGGGG TGAAACAGAA CCAGCAGAAT CTTTGCTTTG ACACAGTGA T GAGGGCAC | 300 |
| CTTGAGGGAG GCAGAAATGG CAAAGAAAGA AATGGGTGCC ATGCAGAGGA A GTCAGTGAA | 360 |
| GATGAGCATG GCCATGCGCT TGGCGATCCT GGTGTCACTA GAGGAGGACA C GATGTTGGG | 420 |
| GTTCCGCACT GTGAGGTAGA TGTGGATATA GCAGCCACAG ATGACCACAA A GGCCAGGAC | 480 |
| ATTGAGCACA AGGAGGGACA TGACATACAG CTGTGACAAA GGGCTGTCAA T ATCCATGGG | 540 |
| CAGGCAGATG CTCACCTTCA TGTAGCTGCT GATGCCAAAG ATGGGAAAGA G GGCAGCTGC | 600 |
| AAAAGCAAAA ATCCAGCCCA TCACCATGAC ACTGGCAGCA TGGCGGAGCT G CACCTTGCA | 660 |
| GTCCAGCTGC ATGGCATGCG TGATGGTATG CCATCTTTCC AAGGTGATAG C TGTCAGAGT | 720 |
| GTAGACTGAC AGCTCACTGG CAAAGACAGT GAAAAAGCCA GCAGCATCAC A GCCTGCCCC | 780 |
| AGTTTGCCAG TCGATCGCAT AGTTGTGATA TTGGCTCTTG GTATGGATAT C AACTGATGC | 840 |
| AATGAGCAGC AGGTAGATTC CAATGCAGAG ATCAGCAAAG GCCAGGTTGC A CATAAGGAA | 900 |
| CCTGGGGACT GTGAGTTTAT ATTGGCTGGT AGTTAGGATC ACTAGCACTA T GATGTTCCC | 960 |
| AGTGATGGCC AGGATGCTGA TAAACCATAT CAGGACTCTG AGGATGTTGT A CCCCAGGTA | 1020 |
| ACCGGAGGCA TCTTCTGAGA TGAATGCAGG AAGTTGTTTT TGAAGAGGAC T GCTTTTATT | 1080 |
| GATGGAGACT AAACTGTATT CAGTTAACCC ACTTTCATTT TTCTCCTCAT C CTCCCAAAA | 1140 |
| GGTGGCATAT CACTTACCTA GGGCCATAGC GTGGCATCAA GCTTGTCGTC G TCGTCCTTG | 1200 |
| TAGTCGCTCA CCACGCCCTG GCACAGCAGC AGGTTGCTCA CCACCAGCAG C AGCAGCAGT | 1260 |
| CTAGATCCCT TCTGGCTCGA GCCCTTGGAG TCCATGGTGG | 1300 |

(2) INFORMATION FOR SEQ ID NO:38:

(i) SEQUENCE CHARACTERISTICS:
        (A) LENGTH: 423 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:38:

Met Asp Ser Lys Gly Ser Ser Gln Lys Gly S er Arg Leu Leu Leu Leu
1             5                 10              15

Leu Val Val Ser Asn Leu Leu Leu Cys Gln G ly Val Val Ser Asp Tyr
        20               25             30

```
Lys Asp Asp Asp Lys Leu Asp Ala Thr Leu Leu Trp Pro Phe Trp
        35                  40                  45

Glu Asp Glu Lys Asn Glu Ser Gly Leu Thr Glu Tyr Arg Leu Val
    50                  55                  60

Ser Ile Asn Lys Ser Ser Pro Leu Gln Lys Gln Leu Pro Ala Phe Ile
65                  70                  75                  80

Ser Glu Asp Ala Ser Gly Tyr Leu Gly Tyr Asn Ile Leu Arg Val Leu
                85                  90                  95

Ile Trp Phe Ile Ser Ile Leu Ala Ile Thr Gly Asn Ile Ile Val Leu
            100                 105                 110

Val Ile Leu Thr Thr Ser Gln Tyr Lys Leu Thr Val Pro Arg Phe Leu
        115                 120                 125

Met Cys Asn Leu Ala Phe Ala Asp Leu Cys Ile Gly Ile Tyr Leu Leu
        130                 135                 140

Leu Ile Ala Ser Val Asp Ile His Thr Lys Ser Gln Tyr His Asn Tyr
145                 150                 155                 160

Ala Ile Asp Trp Gln Thr Gly Ala Gly Cys Asp Ala Ala Gly Phe Phe
                165                 170                 175

Thr Val Phe Ala Ser Glu Leu Ser Val Tyr Thr Leu Thr Ala Ile Thr
            180                 185                 190

Leu Glu Arg Trp His Thr Ile Thr His Ala Met Gln Leu Asp Cys Lys
        195                 200                 205

Val Gln Leu Arg His Ala Ala Ser Val Met Val Met Gly Trp Ile Phe
        210                 215                 220

Ala Phe Ala Ala Ala Leu Phe Pro Ile Phe Gly Ile Ser Ser Tyr Met
225                 230                 235                 240

Lys Val Ser Ile Cys Leu Pro Met Asp Ile Asp Ser Pro Leu Ser Gln
                245                 250                 255

Leu Tyr Val Met Ser Leu Leu Val Leu Asn Val Leu Ala Phe Val Val
            260                 265                 270

Ile Cys Gly Cys Tyr Ile His Ile Tyr Leu Thr Val Arg Asn Pro Asn
        275                 280                 285

Ile Val Ser Ser Ser Asp Thr Arg Ile Ala Lys Arg Met Ala Met
        290                 295                 300

Leu Ile Phe Thr Asp Phe Leu Cys Met Ala Pro Ile Ser Phe Phe Ala
305                 310                 315                 320

Ile Ser Ala Ser Leu Lys Val Pro Leu Ile Thr Val Ser Lys Ala Lys
                325                 330                 335

Ile Leu Leu Val Leu Phe His Pro Ile Asn Ser Cys Ala Asn Pro Phe
            340                 345                 350

Leu Tyr Ala Ile Phe Thr Lys Asn Phe Arg Arg Asp Phe Phe Ile Leu
        355                 360                 365

Leu Ser Lys Cys Gly Cys Tyr Glu Met Gln Ala Gln Ile Tyr Arg Thr
        370                 375                 380

Glu Thr Ser Ser Thr Val His Asn Thr His Pro Arg Asn Gly His Cys
385                 390                 395                 400

Ser Ser Ala Pro Arg Val Thr Asn Gly Ser Thr Tyr Ile Leu Val Pro
                405                 410                 415

Leu Ser His Leu Ala Gln Asn
                420
```

(2) INFORMATION FOR SEQ ID NO:39:

(i) SEQUENCE CHARACTERISTICS:
        (A) LENGTH: 35 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:39:

GTGGTGAGCA ACCCCAATGA TAAATATGAA CCCTT                                    35

(2) INFORMATION FOR SEQ ID NO:40:

(i) SEQUENCE CHARACTERISTICS:
        (A) LENGTH: 12 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:40:

GCTCACCACG CC                                                             12

(2) INFORMATION FOR SEQ ID NO:41:

(i) SEQUENCE CHARACTERISTICS:
        (A) LENGTH: 18 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:41:

Gly Val Val Ser Xaa Xaa Xaa Xaa Xaa Asn Pro Asn Asp Lys Tyr Glu
1               5                   10                  15
Pro Phe (2) INFORMATION FOR SEQ ID NO:42:

(i) SEQUENCE CHARACTERISTICS:
        (A) LENGTH: 19 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:42:

Thr Leu Asp Pro Arg Xaa Xaa Xaa Xaa Xaa Asn Pro Asn Asp Lys Tyr
1               5                   10                  15
Glu Pro Phe (2) INFORMATION FOR SEQ ID NO:43:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:43:

Ser Phe Leu Leu Arg Asn
1               5

(2) INFORMATION FOR SEQ ID NO:44:

(i) SEQUENCE CHARACTERISTICS:
        (A) LENGTH: 429 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:44:

```
Met Asp Ser Lys Gly Ser Ser Gln Lys Gly S er Arg Leu Leu Leu Leu
  1               5                  10                  15

Leu Val Val Ser Asn Leu Leu Leu Cys Gln G ly Val Val Ser Asp Tyr
             20                  25                  30

Lys Asp Asp Asp Lys Leu Asp Ala Thr L eu Asp Pro Arg Xaa Xaa
         35                  40                  45

Xaa Xaa Xaa Asn Pro Asn Asp Lys Tyr Glu P ro Phe Trp Glu Asp Glu
     50                  55                  60

Glu Lys Asn Glu Ser Gly Leu Thr Glu Tyr A rg Leu Val Ser Ile Asn
 65                  70                  75                  80

Lys Ser Ser Pro Leu Gln Lys Gln Leu Pro A la Phe Ile Ser Glu Asp
             85                  90                  95

Ala Ser Gly Tyr Leu Val Leu Tyr Tyr Leu A la Ile Val Gly His Ser
            100                 105                 110

Leu Ser Ile Phe Thr Leu Val Ile Ser Leu G ly Ile Phe Val Phe Phe
            115                 120                 125

Arg Ser Leu Gly Cys Gln Arg Val Thr Leu H is Lys Asn Met Phe Leu
        130                 135                 140

Thr Tyr Ile Leu Asn Ser Met Ile Ile Ile  His Leu Val Glu Val
145                 150                 155                 160

Val Pro Asn Gly Glu Leu Val Arg Arg Asp P ro Val Ser Cys Lys Ile
                165                 170                 175

Leu His Phe Phe His Gln Tyr Met Met Ala C ys Asn Tyr Phe Trp Met
            180                 185                 190

Leu Cys Glu Gly Ile Tyr Leu His Thr Leu I le Val Val Ala Val Phe
        195                 200                 205

Thr Glu Lys Gln Arg Leu Arg Trp Tyr Tyr L eu Leu Gly Trp Gly Phe
    210                 215                 220

Pro Leu Val Pro Thr Thr Ile His Ala Ile T hr Arg Ala Val Tyr Phe
225                 230                 235                 240

Asn Asp Asn Cys Trp Leu Ser Val Glu Thr H is Leu Leu Tyr Ile Ile
                245                 250                 255

His Gly Pro Val Met Ala Ala Leu Val Val A sn Phe Phe Phe Leu Leu
            260                 265                 270

Asn Ile Val Arg Val Leu Val Thr Lys Met A rg Glu Thr His Glu Ala
        275                 280                 285

Glu Ser His Met Tyr Leu Lys Ala Val Lys A la Thr Met Ile Leu Val
    290                 295                 300

Pro Leu Leu Gly Ile Gln Phe Val Val Phe P ro Trp Arg Pro Ser Asn
305                 310                 315                 320

Lys Met Leu Gly Lys Ile Tyr Asp Tyr Val M et His Ser Leu Ile His
                325                 330                 335

Phe Gln Gly Phe Phe Val Ala Thr Ile Tyr C ys Phe Cys Asn Asn Glu
            340                 345                 350
```

-continued

```
Val Gln Thr Thr Val Lys Arg Gln Trp Ala G ln Phe Lys Ile Gln Trp
            355             360             365

Asn Gln Arg Trp Gly Arg Arg Pro Ser Asn A rg Ser Ala Arg Ala Ala
            370             375             380

Ala Ala Ala Ala Glu Ala Gly Asp Ile Pro I le Tyr Ile Cys His Gln
385             390             395             400

Glu Leu Arg Asn Glu Pro Ala Asn Asn Gln G ly Glu Glu Ser Ala Glu
            405             410             415

Ile Ile Pro Leu Asn Ile Ile Glu Gln Glu S er Ser Ala
            420             425
```

What is claimed is:

1. A method of identifying a peptide agonist of a G protein-coupled receptor of interest, said method comprising:
expressing a self-activating fusion protein in a cell, the self-activating fusion protein comprising an amino terminus of a self-activating receptor, a peptide of a synthetic peptide library positioned within the amino terminus of the self-activating receptor, and a G protein-coupled receptor of interest having a deleted amino terminus and monitoring a signaling pathway regulated by the G protein-coupled receptor of interest to determine whether the peptide is an agonist of the G protein-coupled receptor of interest.

2. The method of claim 1 wherein said expressing a self-activating fusion protein comprises:
introducing a fusion protein construct into a cell, the fusion protein construct comprising first, second, and third nucleic acid molecules ligated together in sense orientation for expression of the self-activating fusion protein,
the first nucleic acid molecule encoding the G protein-coupled receptor;
the second nucleic acid molecule encoding the amino terminus of the self-activating receptor, the amino terminus of the self-activating receptor having a deleted portion which includes a peptide sequence of the amino terminus responsible for activating the self-activating receptor, the second nucleic acid molecule being ligated 5' to the first nucleic acid molecule; and
the third nucleic acid molecule encoding the peptide of the synthetic peptide library, the third nucleic acid molecule being ligated to the second nucleic acid molecule such that the peptide of the synthetic peptide library replaces the deleted portion;
allowing the cell to express the self-activating fusion protein encoded by the fusion protein construct; and
exposing the cell to an enzyme of the self-activating receptor, wherein the enzyme cleaves the self-activating fusion protein to expose the peptide of the synthetic peptide library.

3. The method of claim 2 wherein said introducing comprises injecting the fusion protein construct into the cell.

4. The method of claim 2 wherein said introducing comprises transforming the cell with an expression vector comprising the fusion protein construct.

5. The method of claim 1 further comprising:
introducing into the cell a reporter protein construct encoding a reporter protein,
wherein expression of the reporter protein is dependent upon the signaling pathway and said monitoring comprises detecting expression levels of the reporter protein.

6. The method of claim 5 wherein said introducing comprises injecting the fusion protein construct into the cell.

7. The method of claim 5 wherein said introducing comprises transforming the cell with an expression vector comprising the fusion protein construct.

8. The method of claim 1 wherein said expressing a self-activating fusion protein comprises:
introducing a fusion protein construct into a cell, the fusion protein construct comprising first, second, and third nucleic acid molecules ligated together in sense orientation for expression of the self-activating fusion protein,
the first nucleic acid molecule encoding the G protein-coupled receptor;
the second nucleic acid molecule encoding the amino terminus of the self-activating receptor, the amino terminus of the self-activating receptor having a deleted portion which includes a peptide sequence of the amino terminus responsible for activating the self-activating receptor as well as any amino acids positioned amino terminally to the peptide sequence, the second nucleic acid molecule being ligated 5' to the first nucleic acid molecule; and
the third nucleic acid molecule encoding the peptide of the synthetic peptide library, the third nucleic acid molecule being ligated 5' to the second nucleic acid molecule; and
allowing the cell to express the self-activating fusion protein encoded by the fusion protein construct, wherein the peptide of the synthetic peptide library is exposed upon expression of the self-activating fusion protein.

9. The method of claim 8 wherein said introducing comprises injecting the fusion protein construct into the cell.

10. The method of claim 8 wherein said introducing comprises transforming the cell with an expression vector comprising the fusion protein construct.

11. The method of claim 1 wherein the self-activating fusion protein signals through an ion channel pathway and wherein said monitoring comprises detecting levels of an ion within the cell.

12. The method of claim 11 wherein the ion channel pathway is a calcium channel and the ion is calcium.

13. The method of claim 12 wherein the cell is a Xenopus oocyte and wherein said detecting is carried out by voltage clamp analysis.

14. The method of claim 1 wherein the self-activating fusion protein signals through a cyclic adenosine monophosphate pathway and wherein said monitoring comprises detecting levels of cyclic adenosine monophosphate within the cell.

15. A method of identifying a negative antagonist of a constitutively active G protein-coupled receptor of interest, said method comprising:

expressing a self-activating fusion protein in a cell, the self-activating fusion protein comprising an amino terminus of a self-activating receptor, a peptide of a synthetic peptide library positioned within the amino terminus of the self-activating receptor, and a constitutively active G protein-coupled receptor of interest having a deleted amino terminus and monitoring a signaling pathway regulated by the constitutively active G protein-coupled receptor of interest to determine whether the peptide is a negative antagonist of the constitutively active G protein-coupled receptor of interest.

16. The method of claim 15 wherein the self-activating fusion protein signals through an ion channel pathway and wherein said monitoring comprises detecting levels of an ion within the cell.

17. The method of claim 16 wherein the ion channel pathway is a calcium channel pathway and the ion is calcium.

18. The method of claim 17 wherein the cell is a Xenopus oocyte and wherein said detecting is carried out by voltage clamp analysis.

19. The method of claim 16 wherein the self-activating fusion protein signals through a cyclic adenosine monophosphate pathway and wherein said monitoring comprises detecting levels of cyclic adenosine monophosphate within the cell.

20. The method of claim 16 further comprising:

introducing into the cell a reporter protein construct encoding a reporter protein, wherein expression of the reporter protein is dependent upon the signaling pathway and said monitoring comprises detecting expression levels of the reporter protein.

21. The method of claim 15 wherein said expressing a self-activating fusion protein comprises:

introducing a fusion protein construct into a cell, the fusion protein construct comprising first, second, and third nucleic acid molecules ligated together in sense orientation for expression of the self-activating fuision protein, the first nucleic acid molecule encoding the constitutively active G protein-coupled receptor;

the second nucleic acid molecule encoding the amino terminus of the self-activating receptor, the amino terminus of the self-activating receptor having a deleted portion which includes a peptide sequence of the amino terminus responsible for activating the self-activating receptor as well as any amino acids positioned amino terminally to the peptide sequence, the second nucleic acid molecule being ligated 5' to the first nucleic acid molecule; and the third nucleic acid molecule encoding the peptide of the peptide library, the third nucleic acid molecule being ligated 5' to the second nucleic acid molecule and allowing the cell to express the self-activating fusion protein encoded by the fusion protein construct.

* * * * *